Figure 1:
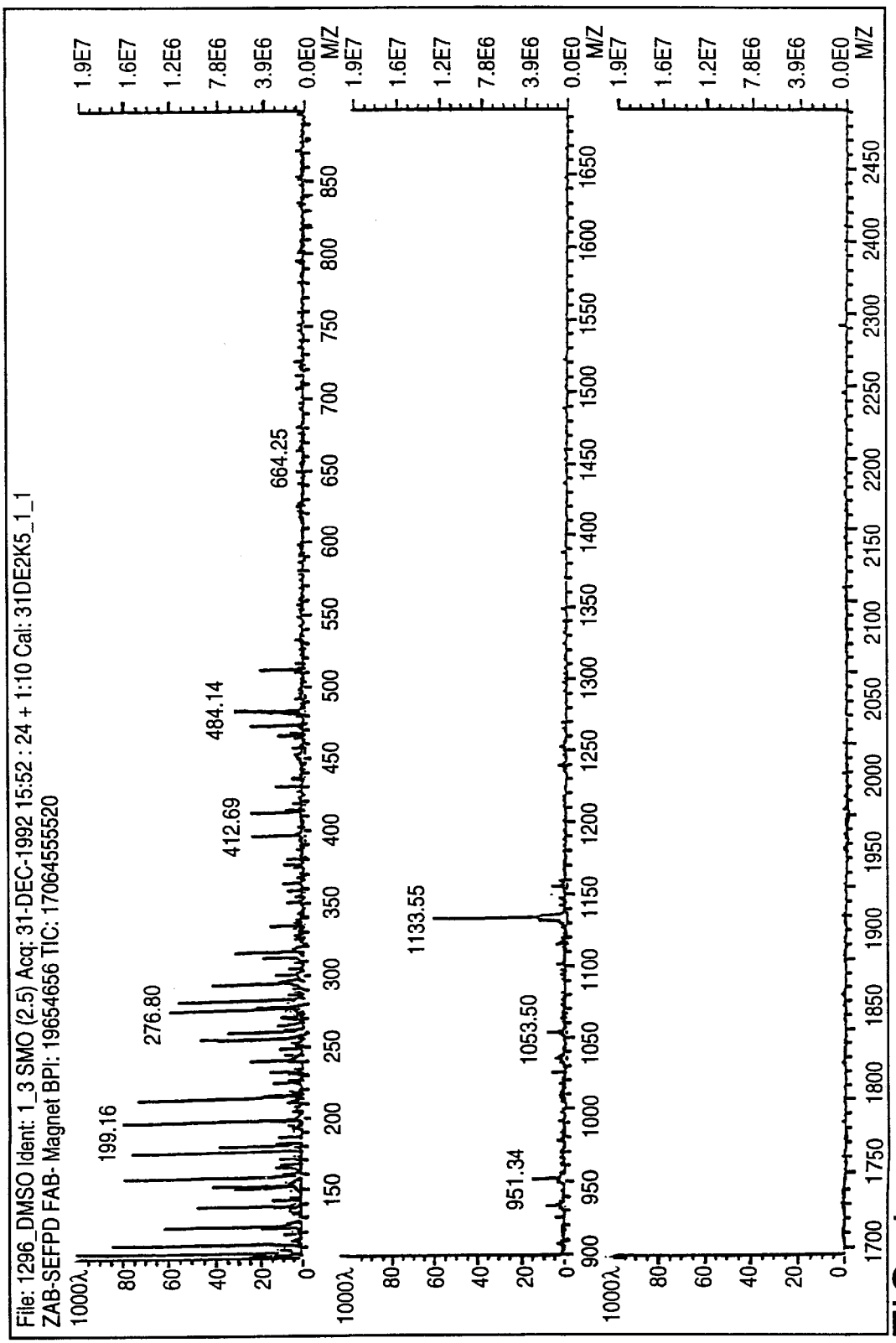

United States Patent [19]
Davies et al.

[11] Patent Number: 6,005,099
[45] Date of Patent: *Dec. 21, 1999

[54] GLUCOSAMINE DISACCHARIDES, METHOD FOR THEIR PREPARATION, PHARMACEUTICAL COMPOSITION COMPRISING SAME, AND THEIR USE

[75] Inventors: John Gwynfor Davies, Woking, United Kingdom; Jacques Bauer, St. Prex, Switzerland; Pierre Hirt, Préverenges, Switzerland; Adrian Schulthess, Begnins, Switzerland

[73] Assignee: Laboratoires OM S.A., Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/648,022

[22] PCT Filed: Nov. 17, 1994

[86] PCT No.: PCT/EP94/03852

§ 371 Date: Sep. 11, 1996

§ 102(e) Date: Sep. 11, 1996

[87] PCT Pub. No.: WO95/14026

PCT Pub. Date: May 26, 1995

[30] Foreign Application Priority Data

Nov. 17, 1993 [EP] European Pat. Off. .............. 93203223

[51] Int. Cl.$^6$ ..................................... C07H 5/04
[52] U.S. Cl. .......................... 536/55.2; 536/55.3; 536/58; 536/62; 514/53; 514/62
[58] Field of Search ....................... 514/53, 62; 536/55.2, 536/55.3, 58, 62

[56] References Cited

PUBLICATIONS

Charon et al. "Chemistry of Bacterial Endotoxins. Part 2. A Practical Synthesis of 6–O–{4–O–Ammonio(hydrogen)phosphono–2–deoxy–2–[(3R)–hydroxytetradecanamido]–β–D–glucopyranosyl}–2–deoxy–2–[(3R)–3–hydroxytetradecanamido]–D–glucose," J. Chem. Soc. Perkin Trans 1, pp. 2291–2295 (1984).

Kusumoto et al., "Chemical Synthesis of 1–Dephospho Derivative of *Escherichia Coli* Lipid A," Tetrahedron letters, vol. 26, No. 7, pp. 909–912 (1985).

Imoto et al., "Total Synthesis of *Escherichia coli* Lipid A, the Endotoxically Active Principle of Cell–Surface Lipoplysaccharide," Bull. Chem. Soc. Jpn., 60, pp. 2205–2214 (1987).

*Primary Examiner*—James O. Wilson
*Attorney, Agent, or Firm*—Webb Ziesenheim Logsdon Orkin & Hanson, P.C.

[57] ABSTRACT

The invention relates to β(1→6) glucosamine disaccharides having general formula (I) to a method for preparing these disaccharides, comprising the steps of: i) providing a starting material comprising lipid A moiety of lipopolysaccharide-comprising microorganisms; and ii) subjecting the starting material to an alkaline treatment such as lipid A moiety is O-deacylated at the 3-position and at the 3'-position, to pharmaceutical compositions comprising as an active ingredient these disaccharides, and to these disaccharides for use as an immunomodulating agent, anti-tumor agent, and vaccine component.

34 Claims, 8 Drawing Sheets

GLUCOSAMINE DISACCHARIDES, METHOD FOR THEIR PREPARATION, PHARMACEUTICAL COMPOSITION COMPRISING SAME, AND THEIR USE

The present invention relates to specific glucosamine disaccharides, in particular to 2-N- and/or 2'-N-acylated glucosamine disaccharides, wherein at least one of the acyl groups is branched, and to compounds comprising these disaccharides. The present invention relates further to methods for preparing these disaccharides from starting materials comprising the lipid A moiety of lipopolysaccharides which starting material is subjected to a specific alkaline treatment. The invention relates also to pharmaceutical compositions comprising these disaccharides as an active ingredient, and finally to the use of these disaccharides in therapy and prophylaxis.

Lipopolysaccharides constitute endotoxins of microorganisms such as Gram-negative bacteria, and comprise a polysaccharide component and a lipid component. This lipid component, also called lipid A, determines the endotoxic properties of lipopolysaccharides (Rietschel E. Th. et al. in Immunobiology, Volume 186, pages 169–190 [1993]).

In U.S. Pat. No. 4,912,094 modified lipopolysaccharides have been disclosed which exhibit reduced endotoxic properties while maintaining their antigenic and immunostimulating properties. These modified lipopolysaccharides are 3-O-deacylated and may be converted into 3-O-deacylated disaccharides by acid hydrolysis. Of these compounds the monophosphoryl 3-O-deacylated disaccharide is less toxic than the diphosphoryl 3-O-deacylated disaccharide.

The present invention relates to disaccharides which are 3-O-deacylated and 3'-O-deacylated or comprise at the 3-O-position and/or the 3'-O-position a short O-linked alkyl or acyl group, and comprise at least an N-linked, branched acyl group at the 2-position, 2'-position, or at both the 2-position and 2'-position. These compounds exhibit a still lower endotoxicity while maintaining biological activity (such as immunomodulation) and possess anti-cancer activity.

It was surprising that these specific glucosamine disaccharides possess the combination of lower endotoxicity and maintained biological activity, because although synthetic 3-O- and 3'-O-deacylated glucosamine disaccharides comprising an N-linked acyl group at the 2- and 2'-position (compound 307, Takada, H. et al. in CRC Critical Reviews in Microbiology, Volume 16, pages 477–523 [1989]; and compound LA-19-PP, Rietschel et al. [1993]) exhibited some immunobiological activities in in vitro assays, these activities were far weaker than those of reference bacterial lipid A specimens. They also lacked typical endotoxic activity.

Accordingly, the present invention relates to β(1→6) glucosamine disaccharides having the general formula

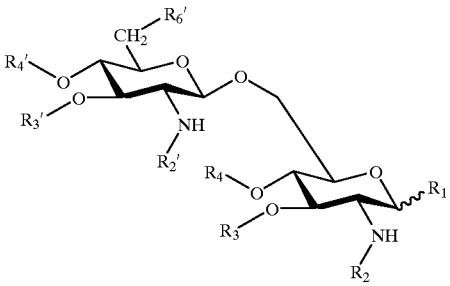

wherein
$R_1$ is a hydroxyl group,
    a dihydroxyphosphonoyloxy group or its charged forms,
    a $(C_1-C_5)$acyloxy group;
    a $(C_1-C_5)$alkyloxy group, or
    a group X;
$R_2$ and $R_2'$ are each an acyl group or a group Y with the proviso that at least $R_2$ or $R_2'$ is the group Y;
$R_3$ and $R_3'$ are each hydrogen,
    a $(C_1-C_3)$alkyl group, or
    a $(C_1-C_3)$acyl group;
$R_4$ is hydrogen,
    a $(C_1-C_3)$alkyl group, or
    a $(C_1-C_3)$acyl group;
$R_4'$ is hydrogen,
    a $(C_1-C_5)$acyl group,
    a $(C_1-C_5)$alkyl group,
    a dimethoxyphosphonoyl group, or
    a phosphono group or its charged forms; and
$R_6'$ is hydrogen,
    a hydroxyl group,
    a dihydroxyphosphonoyloxy group,
    a hydroxysulphonyloxy group, their charged forms, or a group Z;
wherein the group X is selected from the group comprising
    a carboxy $(C_1-C_5)$alkyloxy group;
    an —O—CH—[$(CH_2)_m$COOH][$(CH_2)_n$COOH] group, wherein
    m=0–5 and
    n=0–5;
    a phosphono$(C_1-C_5)$alkyl group;
    a dimethoxyphosphonoyloxy group;
    a hydroxysulphonyloxy group;
    a hydroxysulphonyl$(C_1-C_5)$alkyl group; and
    charged forms of the group X;
wherein the group Y is selected from the group comprising
    an acyloxyacyl group,
    an acylaminoacyl group,
    an acylthioacyl group,
    a $(C_1-C_{24})$alkyloxyacyl group,
    a $(C_1-C_{24})$alkylaminoacyl group,
    a $(C_1-C_{24})$alkylthioacyl group; and
wherein the group Z is selected from the group comprising
    a $(C_1-C_{24})$alkyloxy group;
    a $(C_1-C_{24})$acyloxy group;
    3-deoxy-D-manno-2-octulosonic acid (KDO);

(KDO)$_n$, wherein n=1–10;

a polysaccharide side chain, such as a side chain originating from natural lipopolysaccharide;

a core component, such as a component originating from natural lipopolysaccharide; and amino-(C$_1$–C$_8$)alkyl-carboxyl group;

and its salts.

These glucosamine disaccharides exhibit a far lower endotoxicity, determined in the limulus amoebocyte lysate (LAL) test, than lipopolysaccharides (LPS) from for instance E.coli, lipid A and modified lipid A according to U.S. Pat. No. 4,912,094. Furthermore, these glucosamine disaccharides according to the invention induce nitric oxide reactive intermediates and cytokines, such as interleukin 1-alpha (IL 1-alpha), IL-6, tumor necrosis factor (TNF) and prostaglandin (PGE).

In addition, these disaccharides show anti-tumor activity such as in peritoneal carcinomatosis.

Finally the acute toxicity of these disaccharides is extremely low. No deaths were monitored in Swiss mice after an intravenous dose of 100 mg disaccharide per kg body weight.

The present invention relates also to a method for preparing these glucosamine disaccharides using starting material from biological origin, that is, any starting material comprising the lipid A moiety of polysaccharides from micro-organisms, such as Gram-negative bacteria. According to the invention this starting material is subjected to at least an alkaline treatment such that the sugar O-linked acyl and/or O-linked oxyacyl groups are removed. If appropriate, the alkaline-treated starting material may be subjected to further treatments for removing the polysaccharide and core component (by acid treatment), and for changing or exchanging the substituents at the 1-position, 2-position, 3-position, 4-position, 2'-position, 3'-position, 4'-position and 6'-position.

However, the glucosamine disaccharides according to the invention can also be obtained by synthesis starting from the corresponding glucosamine disaccharide and introduce the objective substituents at the 2- and/or 2'-position.

Due to the extremely low endotoxicity in combination with the above-disclosed biological activity, these disaccharides according to the invention form an elite active ingredient of a pharmaceutical composition. Such a pharmaceutical composition and the disaccharides per se may be used as immunomodulating agent, anti-tumor agent and as a vaccine component.

The glucosamine disaccharide according to the invention (a β(1→6) D-glucosamine dimer) is characterized in that each glucosamine comprises at the 3- and 3'-position a hydroxyl group or a short O-linked alkyl or acyl group not substantially changing endotoxicity and/or biological activity, and further at least one N-linked, branched acyl group at the 2- or 2'-position or at both 2- and 2'-position. The remaining 2'- or 2-position is N-acylated. Presumably the presence of two hydrophobic chains at the 2-position and the 2'-position, at least one of which is in the form of a branched acyl group, imparts the disaccharide with the combination of extremely low endotoxicity and maintained biological activity.

The branched acyl group, herein in general referred to as the group Y is selected from the group comprising an acyloxyacyl group, an acylaminoacyl group, an acylthioacyl group, a (C$_1$–C$_{24}$)alkyloxyacyl group, a (C$_1$–C$_{24}$)alkylaminoacyl group, and a (C$_1$–C$_{24}$)alkylthioacyl group.

In the case of the acyloxyacyl group, the two acyl groups are linked via an oxygen atom, in the case of the acylaminoacyl group via an NH group, and in the case of the acylthioacyl group via a sulphur atom. The other members of the group Y, the (C$_1$–C$_{24}$)alkyloxyacyl group, the (C$_1$–C$_{24}$)alkylaminoacyl group and the (C$_1$–C$_{24}$)alkylthioacyl group may be obtained starting from the corresponding hydroxy fatty acid.

Preferably, the group Y represents an N-linked acyl group branched at its 3-position, such as a 3-acyloxyacyl group, a 3-acylaminoacyl group, and the 3-acylthioacyl group. The same applies to the aforementioned (C$_1$–C$_{24}$)alkyl equivalents.

Preferably the members of the group Y comprise one or two acyl moieties, preferably selected from fatty acid residues, hydroxy fatty acid residues and oxy fatty acid residues. When the acyloxyacyl group is preferably a 3-acyloxyacyl group, these acyl moieties comprise a 3-hydroxy fatty acid residue or for the ester-linked group a 3-oxo fatty acid residue. Typical examples of the acyloxyacyl group are 3-hydroxy(C$_4$–C$_{24}$)-fatty acid-acyls which are ester-linked at the 3-hydroxy position with a (C$_1$–C$_{24}$)-carboxylic acid. Preferably the acyloxyacyl group is a 3-hydroxy(C$_8$–C$_{18}$)-fatty acid-acyl which is ester-linked at the 3-hydroxy position with (C$_{10}$–C$_{18}$)-fatty acid. Such acyloxyacyl groups are present in the lipid A component of Gram-negative bacteria, such as *Escherichia coli, Haemophilus influenzae, Campylobacter jejuni, Rhodocyclus gelatinosus, Chromobacterium violaceum, Neisseria meningitidis, Salmonella minnesota.*

In a first group of preferred glucosamine disaccharides according to the invention the acyloxyacyl group is the N-linked 3-hydroxyC$_{14}$-fatty acid-acyl ester-linked at the 3-hydroxy position with the C$_{12}$-fatty acid, with this acyloxyacyl group at the 2'-position. In another preferred glucosamine disaccharide according to the invention the acyloxyacyl group is the N-linked 3-hydroxyC$_{14}$-fatty acid-acyl ester-linked at the 3-hydroxy position with the C$_{14}$-fatty acid, and the acyloxyacyl group is preferably at the 2'-position.

In another preferred glucosamine disaccharide according to the invention the acyloxyacyl group is the N-linked 3-hydroxyC$_{14}$-fatty acid-acyl ester-linked at the 3-hydroxy position with the C$_{12}$-fatty acid, with this acyloxyacyl group at the 2-position. In another preferred glucosamine disaccharide according to the invention the acyloxyacyl group is the N-linked 3-hydroxyC$_{14}$-fatty acid-acyl ester-linked at the 3-hydroxy position with the C$_{12}$-fatty acid, with the acyloxyacyl group at both the 2-position and the 2'-position.

When the group Y comprises a chiral centre the invention encompasses all R- and S enantiomers, and any racemic mixture.

The other N-linked substituent may be an acyl group or also an acyloxyacyl group. According to a second group of disaccharides according to the invention the acyl group is a 3-hydroxy(C$_4$–C$_{24}$)-fatty acid, preferably a 3-hydroxy (C$_{10}$–C$_{18}$)-fatty acid. In the preferred disaccharides according to the invention the acyl group is a 3-hydroxyC$_{14}$-fatty acid, at the 2-position or at the 2'-position.

However, the N-linked substituent may also be an acyloxyacyl group defined hereinbefore, and comprising an N-linked 3-hydroxy(C$_4$–C$_{24}$)-fatty acid-acyl which is ester-linked at the 3-hydroxy position with (C$_1$–C$_{20}$)-carboxylic acid, preferably an N-linked 3-hydroxy(C$_8$–C$_{18}$) -fatty acid-acyl ester-linked at the 3-hydroxy position with (C$_{10}$–C$_{18}$)-fatty acid. More preferred is the disaccharide wherein R$_2$ is the N-linked 3-hydroxyC$_{14}$-fatty acid-acyl ester-linked at the 3-hydroxy position with the C$_{12}$-fatty acid or C$_{16}$-fatty acid, and wherein R$_2$' is the N-linked 3-hydroxyC$_{14}$-fatty acid-acyl ester-linked at the 3-hydroxy position with the $C_{12}$-fatty acid or $C_{14}$-fatty acid.

It is noted, that in the group Y the acyl groups and/or the acyl and alkyl group may be interlinked.

In this specification the term "fatty acid residue" means: a substantially hydrophobic chain of $C_2$–$C_{30}$ atoms, which chain may be straight, branched, saturated, mono- or poly-unsaturated, having inserted one or more hetero atoms such as nitrogen, oxygen, sulphur, and which chain may be substituted with one or more substituents, such as hydroxyl, oxo, acyloxy, alkoxy, amino, nitro, cyano, halogeno, sulphydryl, provided that the biological activity is not substantially adversely affected. An example of a substituted fatty acid residue (comprising an amide-linked substituent) is disclosed by Onozuka, K. et al. in Int. J. Immunopharmac, Volume 15, pages 657–664 [1993]).

The substituent $R_1$ may be a $(C_1$–$C_5)$acyloxy group or a $(C_1$–$C_5)$alkyloxy group while $R_4'$ may be a $(C_1$–$C_5)$acyl group or a $(C_1$–$C_5)$alkyl group, provided that the properties of the glucosamine disaccharides are not adversely affected. Furthermore, $R_1$ may be an hydroxyl group and $R_4$ may be hydrogen. Preferably, $R_1$ and $R_4'$ may each be a phosphorus containing group. In particular such a group at the 1-position or 4'-position may influence the biological activity, such as a different stimulation of cytokines (see Takada, H., and Kotani, S., in Bacterial Endotoxic Lipopolysaccharides, Morrison, D. C. and Ryan, J., CRC Press, Volume 1, pages 107–134 [1992], in particular page 123). The preferred disaccharides according to the invention comprise a dihydroxyphosphonoyloxy group at the 1-position and a phosphono group at the 4'-position, which group for the 1-position is preferably in the α-configuration.

The substituent $R_1$ may also be represented by the group X. The group X is generally negatively charged at physiological pH. The group X may be a carboxy $(C_1$–$C_5)$ alkyloxy group. The group X may also be a dicarboxylic acid with the formula —O—CH—[$(CH_2)_m$COOH][$(CH_2)_n$COOH], wherein m=0–10 and n=0–10, such as m and n=0, m and n=1; and m=1 and n=3. The dicarboxylic acid substituent at the 1-position wherein m and n=1 is disclosed by Onozuka et al. (1993). Instead of a dicarboxylic acid the group X may be represented by a phosphono $(C_1$–$C_5)$-alkyl group, such as a phosphonomethyl group or a phosphonoethyl group.

The substituent group X may also have the form of a sulphate group or a hydroxysulphonyl $(C_1$–$C_5)$-alkyl group, such as a hydroxysulphonylmethyl group.

The substituents $R_3$ and $R_3'$ may be a short alkyl or acyl group, which do not adversely affect the endotoxicity and/or biological activity of the glucosamine disaccharides according to the invention. Examples are a $(C_1$–$C_3)$alkyl group, and a $(C_1$–$C_3)$acyl group. Preferably, the substituents $R_3$ and $R_3'$ are both hydrogen, that means that the 3-position and the 3'-position are not acylated.

The substituent $R_4$ at the 4-position may be a $(C_1$–$C_3)$ alkyl group or a $(C_1$–$C_3)$acyl group of which the meaning has been defined hereinbefore. The 4-O-acylated disaccharide may be synthesized using the method disclosed by Kusumoto S., et al., ACS Symposium Series, Volume 231, pages 237–254, (1983). However, preferred is at the 4-position a hydroxyl group ($R_4$=H).

The substituent $R_6'$ may be hydrogen, an hydroxyl group, a dihydroxyphosphonoyloxy group, a dihydroxysulphonyloxy group and their charged forms.

In order to improve the water-solubility of the glucosamine disaccharides according to the invention, the substituent at the 6'-position may have a pronounced hydrophilic character imparted by the group Z. The group Z may be 3-deoxy-D-manno-2-octulosonic acid (KDO) or several KDO molecules, such as present in the inner core of natural polysaccharides directly adjacent to the lipid A component.

The group Z may also be the complete or partial polysaccharide chain, such as a side chain originating from natural lipopolysaccharide, or a core component originating from natural lipopolysaccharides.

The group Z may also be an amino-$(C_1$–$C_8)$alkyl-carboxyl group.

The water-solubility of the disaccharides according to the invention is on the one hand determined by the presence of charged group, the hydrophilic character of the substituent at the 6'-position. On the other hand, the water-solubility may also be improved when the glucosamine disaccharide is in the form of a salt, such as a salt comprising one or more alkali metal cations and/or ammonium ion forming a pair with for instance, dihydroxyphosphonoyloxy groups, carboxylate groups, phosphono groups, hydroxysulphonyloxy groups, and hydroxysulphonylalkyl groups when present.

It is noted that any alkyl and acyl chain or moiety may be straight, branched, saturated, mono- or poly-unsaturated, having inserted one or more hetero atoms such as nitrogen, oxygen, sulphur, and which chain may be substituted with one or more substituents, such as hydroxyl, oxo, acyloxy, alkoxy, amino, nitro, cyano, halogeno, sulphydryl, provided that the biological activity is not substantially adversely affected.

The glucosamine disaccharides according to the invention may be obtained from starting material comprising the lipid A moiety of lipopolysaccharides which are present in micro-organisms, such as Gram-negative bacteria. These lipopolysaccharides are for instance present in a surface structure comprising fraction of these micro-organisms and in lipopolysaccharides originating therefrom. Preferred Gram-negative bacteria used as a source for starting material are *Escherichia coli* and *Haemophilus influenzae*. However, commercially available LPS or lipid A may be used as starting material.

The selective deacylation at the 3-position and at the 3'-position is carried out using an alkaline treatment. The conditions of the alkali treatment are chosen such that both glucosamines are 3-hydroxy deacylated. The alkaline treatment may be carried out using hydroxides, carbonates, and phosphates, such as sodium hydroxide or potassium carbonate. Illustrative organic alkaline agents are alkyl amines, such as diethylamine and triethylamine. The alkaline treatment is normally carried out in an aqueous or organic medium. The pH is typically within the range of 10–14, such as 11–13, under practical conditions the pH is for instance 12.2. The alkaline treatment is normally carried out at a temperature between ambient temperature and 70° C., such as 37° C. The time period depends on the type of starting material. Starting from micro-organisms the time period varies between 1 hour and 10 days, such as 8 hours and 5 days, but is normally within the range of 8–40 hours. Starting from lipopolysaccharides or lipid A the time period may be 0.2–10 hours, such as 1–5 hours. In practice the time period is about 1.5 to 3 hours.

When the starting material comprises at the 6'-position a core component that is to be removed, the starting material is to be subjected to an acid treatment for removing that core component. This acid treatment may be carried out before or after the afore-mentioned alkaline treatment. The acid treatment is carried out at a pH of 1–5, preferably in a pH range of 2.5–4.5, normally at a pH higher than 3 and lower than 4.5, such as 3.5. At pH 1 or below the glucosamine disaccharide is dephosphorylated, resulting in the monophosphorylated form. Acids that might be used are mineral and organic acids, such as hydrochloric acid and glacial acetic acid. The time period for the acid treatment is about 30 minutes to 5 hours, such as 1–2 hours. During the acid treatment the temperature is increased to about 70–100° C., such as 80–100° C., in practice 95° C. Subsequently the temperature is decreased to ambient temperature.

The glucosamine disaccharides according to the invention may also be obtained starting from the corresponding de-, mono-, or di-phosphorylated glucosamine dimer by attaching an acyloxyacyl group, acylaminoacyl group and/or an acylthioacyl group at both the 2-position and 2'-position.

Following partial deacylation of these glucosamine disaccharides according to the invention and separation of the products glucosamine disaccharides are obtained having the branched acyl group at the 2-position or at the 2'-position.

The glucosamine disaccharides according to the invention may be used in a pharmaceutical composition or medicament and used as an immunomodulating agent for inhibiting, stimulating or inducing the tolerisation of the production of nitric oxide reactive intermediates and cytokines, depending on the frequency of application and on the dosage, as anti-tumor agent, as for instance T-cell reactivation, as a vaccine component, as a competitor for endotoxin binding sites and as a modulator of interleukins. Due to the extremely low endotoxicity these disaccharides are almost or substantially free of side effects.

The disaccharides according to the present invention may be applied systemically or locally using intravenous injection, subcutaneous injection, intraperitoneal injection, intramuscular injection, and the like. The dosage will vary depending on the animal or human patient, age, body weight, symptoms or disease to be treated, the desired therapeutic effect, the administration route, term of treatment, and the like. Satisfactory effects will be obtained using a dosage of 0.001 to 500 mg/kg body weight administered in one or more daily doses or as a sustained release form.

The pharmaceutical composition may comprise a pharmaceutically acceptable carrier or diluent for, for instance, non-oral administration of aqueous or non-aqueous solutions, suspensions and emulsions. Aqueous solutions or suspensions may comprise distilled water or physiological saline. Non-aqueous solutions may include propylene glycol, polyethylene glycol, vegetable oils, such as olive oil, alcohols. The composition may contain other additives, such as preservatives, wetting agents, emulsifying agents, dispersing agents and the like.

For a more complete understanding of the present invention reference is made to the following examples, which are provided herein for the purpose of illustration only, and are not intended to limit the scope of the present invention.

EXAMPLE 1

*Escherichia coli* I-1147 (deposited at CNCM on Oct. 3, 1991 under number I-1147) was cultured in a culture medium of which the composition is disclosed in table 1.

TABLE 1 compostion of the culture medium (dissolved in water) for *E. coli* I-1147

| Substance | amount/L |
| --- | --- |
| Inosine | 0.200 g |
| Citric acid monohydrate | 0.300 g |
| Glutamic acid | 1.300 g |
| Ammonium chloride | 1.050 g |
| Magnesium sulphate *7H$_2$O | 1.110 g |
| Potassium dihydrogen phosphate (KH$_2$PO$_4$) | 1.360 g |
| Arginine | 0.300 g |
| Uracil | 0.100 g |
| Calcium chloride | 0.017 g |
| Sodium chloride | 2.000 g |
| Oligometals (stock 1000X conc) | 1 ml |
| L-Leucine | 10.0 g |
| L-Lysine.HCL | 10.0 g |
| L-Serine | 10.0 g |
| L-Methionine | 10.0 g |
| L-Valine | 10.0 g |
| L-Alanine | 10.0 g |
| L-Asparagine | 10.0 g |
| Glucose (Stock 500 g/l) | 5 ml |

Oligometals stock solution: 2.5 g FeCl$_2$.4H$_2$O, 0.25 g CoCl$_2$.6H$_2$O, 0.25 g NaMoO$_4$.7H$_2$O, 0.25 g MnSO$_4$.4H$_2$O, 0.25 g ZnSO$_4$.7H$_2$O, 0.25 g NiSO$_4$.7H$_2$O, 0.05 g H$_3$BO$_4$, 0.05 g CuSO$_4$, then add 1.0 L H$_2$O, mix and add 1.1 ml H$_2$SO$_4$ (85%).

The pH of the culture medium was adjusted using 5N NaOH, 5% ammonia or 25% HCL. Under aeration and stirring (500 rpm) *Escherichia coli* I-1147 was cultured at 37° C. and a pH of 6.9.

Subsequently the content of the fermentor was inactivated using a thermal treatment (105° C. for 2 minutes).

The inactivated content of the fermentor was ultrafiltrated (cut-off 1000 kD), and the retained bacteria were washed using an aqueous 0.6% NaCl solution. The washed bacterial suspension was concentrated by ultrafiltration. Biomass yield 764 g dry weight.

The biomass was diluted to 7.0 g/l and subjected to an alkali treatment by adding 345 ml 10.77 N NaOH and incubated at 37° C. for 40 hours (pH 12.2).

The alkaline extract was subjected to a first ultrafiltration (cut-off 1000 kD), and to a second ultrafiltration of the permeate (10 kD). The retentate of the second ultrafiltration was subjected to an acid treatment.

The retentate was diluted with 7.0 l water and acidified using 370 ml glacial acetic acid (final pH 3.52). The mixture was heated to 95° C. during 120 minutes while stirring. Subsequently the acid suspension was cooled to 25° C. The precipitate was separated by centrifugation (4000×g during 50 minutes). The pellet was resuspended in water (3.7 l) and subjected to an extraction using propan-2-ol (4.3 l) and after 60 minutes at 25° C., 252 ml triethylamine was added (pH 9.0) and stirring was continued for 24 hours.

The supernatant was recovered by centrifugation (4000× g, 25° C. for 50 minutes) and the pellet was re-extracted two times using propan-2-ol 90%. The supernatants were combined and subjected to reversed-phase chromatography (Waters No. 10001, Preparative C$_{18}$, 125 Å).

Alternatively, the acid-treated extract was subjected to ultrafiltration and the retentate (>1000 kD) was concentrated and dialyzed against 5 volumes water. The dialyzed retentate was diluted with 9 volumes propan-2-ol and adjusted to pH 9 with triethylamine (TEA). The extraction was carried out under stirring during 2 hours.

The supernatant is removed as described above and the precipitate is re-extracted with propan-2-ol. The supernatants are combined and subjected to vacuum concentration (40° C., 12 Torr) and finally subjected to reversed-phase chromatography $C_{18}$ Prep Sep Pak (Waters No. 10001).

Each of the two supernatants is diluted with two volumes of water and mixed with 5 mM tetrabutylammonium phosphate (TBAP) and applied to a column comprising 50 g reversed-phase $C_{18}$ Prep Sep Pak (Waters No. 10001, Preparative $C_{18}$, 125 Å) preconditioned with 250 ml $CH_3CN:H_2O$ 1:1, (v/v)+5 mM TBAP. The column was washed with 60% $CH_3CN:H_2O$ 1:1, (v/v)+5 mM TBAP and 40% propan-2-ol:$H_2O$ 9:1, (v/v)+5 mM TBAP. The disaccharides according to the invention eluted in a fraction at 30% $CH_3CN:H_2O$ 1:1, (v/v)+5 mM TBAP and 70% propan-2-ol:$H_2O$ 9:1, (v/v)+5 mM TBAP.

The disaccharide fraction obtained in reversed phase chromatography is diluted with water 1:1 (v/v)+25 mM TBAP and applied to a preparative HPLC column (Millipore-Waters Bondapak C18 300 Å 15M, 300 mm×47 mm φ). The disaccharide fraction according to the invention eluted at 67% propan-2-ol:$H_2O$ 9:1, (v/v)+25 mM TBAP and 33% $CH_3CN:H_2O$ 1:1, (v/v)+25 mM TBAP. This fraction contained 55 mg of disaccharide A according to the invention.

Desalting of the disaccharide

Salt was eliminated from an aliquot of the disaccharide A fraction as follows. A Sep Pak Vac $C_{18}$ Plus column (silica $C_{18}$, 0.6 ml, Waters No. 20515) was conditioned by successively injecting 5 ml of $CHCl_3$—$CH_3OH$ 2:1, (v/v), 5 ml of $CH_3CN$ and 5 ml of $CH_3CN:H_2O$ 1:1, (v/v). The sample was added to the column after dilution of the HPLC fraction with 3 volumes of $H_2O$, giving a total of 6 ml of diluted sample. The TBAP was then eliminated with 10 ml of $CH_3CN:H_2O$ 1:1, (v/v)+10 ml mM HCl, followed by 10 ml of $CH_3CN$. The pure disaccharide A was then removed with 5 ml of $CHCl_3$—$CH_3OH$ 2:1, (v/v).

The fraction was dried by evaporation under vacuum (12 Torr) at 35° C. The desalted disaccharide A was redissolved in $H_2O$:TEA 1000:1, (v/v) for biological and biochemical tests or in chloroform:methanol 2:1, (v/v) for FAB-MS.

Preparation of the sodium salt form

A column comprising 10 g reversed-phase $C_{18}$ Prep Sep Pak (Waters No. 10001, Preparative $C_{18}$, 125 Å) was preconditioned successively with 50 ml of $CH_3CN$ and 50 ml of $CH_3CN:H_2O$ 1:1, (v/v).

The sample (HPLC fraction) was added to the column after dilution with 1 volume of $H_2O$. After adsorption, the column was washed with 100 ml of $CH_3CN:H_2O$ 1:1, (v/v)+5 mM TBAP. The disaccharide was then removed with 50 ml of propan-2-ol:$H_2O$ 9:1, (v/v)+5 mM TBAP.

The resulting fraction was purified as follows. A column comprising 20 ml Q-Sepharose fast flow (Pharmacia 17-0510-01) was conditioned successively with 30 ml of NaOH 1M, washed with $H_2O$ to neutralize, with 30 ml of HCl 1M and washed with $H_2O$ to neutralize.

The sample was applied directly to the column. After adsorption the non adsorbed material was eliminated with 200 ml $H_2O$ and 100 ml propan-2-ol:$H_2O$ 9:1, (v/v). The disaccharide was eluted with 100 ml of NaCl 0.9%:isopropanol 1:1, (v/v).

The final purification was effected as follows. A column comprising 10 g reversed-phase $C_{18}$ Prep Sep Pak was preconditioned successively with 50 ml of $CH_3CN$, 50 ml of $CHCl_3$—$CH_3OH$ 2:1, (v/v), 50 ml of $CH_3CN$ and 50 ml of 50% $CH_3CN:H_2O$ 1:1, (v/v). The sample was added to the column after dilution with 1 volume of $H_2O$. After adsorption, the column was washed successively with 200 ml of $H_2O$, 200 ml of propan-2-ol:$H_2O$ 9:1, (v/v) and 50 ml of $CH_3CN$. The disaccharide was eluted with 50 ml $CHCl_3$—$CH_3OH$ 2:1, (v/v). The fraction was dried by evaporation under vacuum (12 Torr) at 35° C.

The sodium salt was freely soluble in water (up to 100 mg/ml).

EXAMPLE 2

Haemophilus influenzae (purchased from National collection of Type Cultures (ATCC 9795)) was cultured in a culture medium of which the composition is disclosed in table 2.

TABLE 2

| Composition of the main culture medium for Haemophilus influenzae | |
|---|---|
| Substance | Amount/l |
| Sodium chloride | 2 g |
| Sodium monohydrogen phosphate | 2 g |
| Sodium acetate | 0.5 g |
| Aneurine | 0.003 g |
| Nicotinic acid | 0.003 g |
| 70% sodium lactate solution | 2 ml |
| 60% ammonium lactate solution | 2 ml |
| Meat extract | 7.5 g |
| Peptone | 15 g |
| Soya peptone | 1 g |
| Tryptone | 3 g |
| Yeast extract | 7.5 g |
| Glucose | 3 g |

The culture medium was supplemented with hemine (10 mg/l) and NADH (4 mg/l). The pH is adjusted to 7.0±0.3 using 5 N NaOH or 25% HCl. After the beginning of the formation of a stationary phase culturing was interrupted and the content of the fermentor was inactivated by a thermal treatment (100° C. for 100 seconds). The inactivated culture was subjected to centrifugation and the separated biomass was diluted with 0.6% aqueous NaCl solution (approximately 60 g/l). The alkaline treatment was carried out by adding 10 N NaOH to a final concentration of 0.2 N NaOH. The treatment is carried out at 37° C. for 5 days under continuous stirring.

The alkaline-treated lysate was directly subjected to an acid treatment after acidification to pH 3.5 using glacial acetic acid. The mixture is heated to 95° C. for 120 minutes and subsequently cooled to room temperature.

The precipitate was centrifuged (10,000×g, 30 minutes at 4° C.) and the supernatant discarded.

The precipitate was resuspended in $CH_3CN:H_2O$ 1:1, (v/v) and the pH was adjusted to pH 9 using TEA. After centrifugation (15,000×g, 10 minutes) the supernatant was adjusted to 5 mM TBAP. The supernatant is applied to a Sep Pak Vak $C_{18}$ column (10 g silica $C_{18}$, 35 ml, Waters No. 43345) conditioned using 50 ml $CH_3CN:H_2O$) 1:1, (v/v). The fraction containing disaccharide B according to the invention was eluted with 50 ml propan-2-ol:$H_2O$ 9:1, (v/v)+5 mM TBAP.

This fraction was concentrated by evaporation (35° C., 12 Torr) to about 2 ml. The fraction was centrifuged (15,000×g, 5 minutes) and the supernatant was applied to a semi-preparative HPLC $C_{18}$ column (Macherey-Nagel No. 715806, 250 mm×10 mm φ, Nucleosil 300-7C18). The fraction containing disaccharide B according to the invention eluted in a fraction comprising 28% $CH_3CN:H_2O$ 1:1, (v/v)+25 mM TBAP and 72% propan-2-ol:$H_2O$ 9:1, (v/v)+25 mM TBAP.

Disaccharide B was desalted using a method similar to that of example 1.

EXAMPLE 3

Lipopolysaccharide of *Escherichia coli* O111:B4 (Sigma, Product No. L3024) was subjected to an alkaline treatment in 0.2 M NaOH at 37° C. during 1.5 hours. The solution was neutralized using 1 M phosphoric acid.

400 μl of the alkaline treated LPS solution was concentrated by ultrafiltration (Millipore Ultrafree-MC, UFC3 LGC 00, cut-off 10 kD).

The retentate (>10 kD) was diluted in 400 μl $H_2O$ and subjected to an acid treatment by adjusting to 0.2 M acetic acid using glacial acetic acid. The acidified solution was heated to 95° C. for 120 minutes. After cooling to 25° C. the precipitate was sedimented by centrifugation (15,000×g, 10 minutes) and the supernatant was discarded. The precipitate was dissolved in 20 μl $H_2O$:TEA 1000:1, (v/v) and this solution was applied to an analytical HPLC $C_{18}$ column (Supelco No. 58985, Supelcosil LC-18, 3 μm, 150 mm×4,6 mm φ). The disaccharide fraction according to the invention eluted in a fraction comprising 42% $CH_3CN:H_2O$ 1:1, (v/v)+5 mM TBAP and 58% propan-2-ol:$H_2O$ 9:1, (v/v)+5 mM TBAP.

EXAMPLE 4

A solution of 2 mg/ml lipid A of *Escherichia coli* F-583 (Sigma, Product No. L5399) was prepared in $H_2O$:TEA at 1000:1, (v/v), and this solution was subjected to an alkaline treatment using 0.2 M NaOH at 37° C. during 2.5 hours. The solution was neutralized using 1 M phosphoric acid.

The neutralized solution was applied to an analytic HPLC column (Supelco No. 58958, Supelcosil LC-18, 3 μm, 150 mm×4.6 mm φ). The disaccharide according to the invention eluted at 42% $CH_3CN:H_2O$ 1:1, (v/v)+5 mM TBAP and 58% propan-2-ol:$H_2O$ 9:1, (v/v)+5 mM TBAP.

EXAMPLE 5

2-Amino-2-deoxy-6-O-(2-amino-2-deoxy-4-O-phosphono-β-D glucopyranosyl)-α-D-glucopyranosyl dihydrogenphosphate [Holst et al. Eur. J.Biochem. 214 (1993) 695–701] is treated in methanol with sodium methoxide (exactly 4.0 mol. equiv.) and then with (R)-3-dodecanoyloxytetradecanoic anhydride (2.2 mol. equiv.) [prepared by the reaction of (R)-3-dodecanoyloxytetradecanoic acid with DCC (0.5 mol. equiv.) in anhydrous dichloromethane, see Charon et al. J. Chem. Soc. Perkin Trans. I. (1984) 2291–2295]. After 12 hours at room temperature, water is added (2×volume of methanol) and the mixture is extracted with diethyl ether (to remove 3-dodecanoyloxytetradecanoic acid). The aqueous phase is concentrated and the crude disaccharide C according to the invention is subjected to reversed-phase HPLC. The product is dissolved in $H_2O$:TEA 1000:1, (v/v) and tetrabutylammonium phosphate [TBAP] added to a concentration of 5 mM. This solution is then applied to a preparative HPLC column (Millipore-Waters Bondapak C18 300 Å 15M, 300 mm×47 mm φ). Disaccharide C is eluted with a gradient $CH_3CN:H_2O$ 1:1 (v/v)+25 mM TBAP (solvent A) and propan-2-ol:$H_2O$ 9:1 (v/v)+25 mM TBAP (solvent B) (50% A/50% B to 0% A:100% B at 1%/min, flow 80 ml/min.). Desalting is achieved as follows. The HPLC fraction containing disaccharide C is diluted with water then applied to a $C_{18}$-Sep Pak Vac Plus column (Waters) [C18 reversed-phase silica gel preconditioned successively with $CHCl_3$:$CH_3OH$ 2:1 (v/v), $CH_3CN$, $CH_3CN:H_2O$ 1:1 (v/v)]. TBAP is eliminated by washing successively with $CH_3CN:H_2O$ 1:1 (v/v), 10 mM HCl and $CH_3CN$. Pure disaccharide C is eluted with $CHCl_3$:$CH_3OH$ 2:1 (v/v).

EXAMPLE 6

The aqueous phase containing disaccharide C obtained in Example 5 (before purification) is treated with aqueous sodium hydroxide (exactly 1.0 mol. equiv.; concentration leading to an initial pH of 12.5); after 24 hours at room temperature the mixture is adjusted to pH 6.5 to 7 and applied to a preparative HPLC column (Millipore-Waters Bondapak C18 300 Å 15M, 300 mm×47 mm φ). The disaccharides A and D are eluted with a gradient $CH_3CN:H_2O$ 1:1 (v/v)+25 mM TBAP (solvent A) and propan-2-ol:$H_2O$ 9:1 (v/v)+25 mM TBAP (solvent B) (75% A:25% B to 0% A:100% B at 1%/min, flow 80 ml/min). The HPLC fractions containing disaccharides A and D are desalted as described for disaccharide C in example 5.

Comparative example (not according to the invention)

A solution of 10 mg/ml lipid A from *Escherichia coli* F-583 (Sigma Product No. L5399) was prepared in $H_2O$:triethylamine at 1000:1, (v/v) and subsequently subjected to an alkaline treatment with 0.2 M NaOH at 37° C. for 20 minutes. This time period was sufficient to only 3-O deacylate lipid A (Myers et al. in Cellular and Molecular Aspects of Endotoxin Reactions, pages 145–156 [1990], Elsevier Science Publishers).

The solution was neutralized with orthophosphoric acid. For biological assays it was diluted into 0.1% TEA/0.9% NaCl and used without further purification.

For FAB-MS a sample of this alkali-treated lipid A was purified by reversed-phase HPLC (Supelco No. 58985, Supelcosil LC18, 3 μm, 15 mm×4.6 mm φ). A major peak eluting at 18% $CH_3CN:H_2O$ 1:1, (v/v)+5 mM TBAP and 82% propan-2-ol:$H_2O$ 9:1, (v/v)+5 mM TBAP was desalted under conditions described in example 1. The FAB-MS analysis gave a molecular ion of 1570.1 mass units (calculated 1569.1 mass units).

Physico-chemical characteristics of disaccharides according to the invention

The disaccharides A and B obtained in examples 1 and 2 have been subjected to physicochemical characterizations.

Glucosamine was determined after acid hydrolysis (4 M HCL, 16 hours, 100° C., argon atmosphere) and derivatisation using phenyl isothiocyanate and subsequent quantitative analysis by HPLC (see Anumula, K. R. et al, Analytical Biochemistry, Volume 179, pages 113–122 [1991]).

Total fatty acids were determined after acid hydrolysis (4 M HCl, 4 hours, 100° C.) by methylation using $BF_3$ in the presence of methanol and quantitative determination by gas chromatography (column OV-1, Hewlett Packard) (see Miller, L., Gas-Liquid Chromatography of Cellular Fatty Acids as a Bacterial Identification Aid, Gas Chromatography Application Note, pages 228–237 [1984]).

Ester-linked fatty acids were determined by gas chromatography after treatment using $NaOCH_3$ (see Rietschel, E. T. et al, European Journal of Biochemistry, Volume 28, pages 166–173 [1972]).

Phosphate was determined according to the method of Ames (see Ames, B. N., Methods in Enzymology, Volume 8, page 115–118 [1966]).

3-Deoxy-D-manno-2-octulosonic acid (KDO) was determined using the method of Karkhanis, Y. D. et al. (Analytical Biochemistry, Volume 58, pages 595–601 [1978]).

A solution of disaccharide A comprised 2.1 μmol/ml phosphate, 1.9 μmol/ml glucosamine, 1.0 μmol/ml $C_{12:0}$ fatty acid and 2.2 μmol/ml $3OH\text{-}C_{14:0}$ fatty acid. Only the $C_{12:0}$ fatty acid was detected after release of ester-linked fatty acid residues, showing that the $3OH\text{-}C_{14:0}$ fatty acid residues were amide linked. KDO was not detected (<1 mol per 10 mol disaccharide A).

Accordingly, the disaccharide contains per mole, 2 moles of phosphate, 2 moles glucosamine, 2 moles $3OH\text{-}C_{14:0}$ fatty acid and 1 mole $C_{12:0}$ fatty acid.

The fast atom bombardment mass spectroscopy (FAB-MS), negative mode of the sample in $CHCl_3\text{:}CH_3OH$ 1:1, (v/v), concentration 1 mg/ml. A VG ZAB-2SE mass spectrometer set at $V_{acc}$ 8 kV was used to generate a spectrum at 30 kV and an emission current of 1 μA. The spectrometer is calibrated using cesium iodine. The FAB-MS spectrum is given in FIG. 1. Disaccharide A shows a molecular peak at 1133.55 mass units (calculated mass 1133,3). Other peaks suggest a fragmentation of the product during analysis. The peak 1053.5 represents the loss of a phosphate group and 951.3 the loss of the $C_{12}$ fatty acid.

Figure 2:
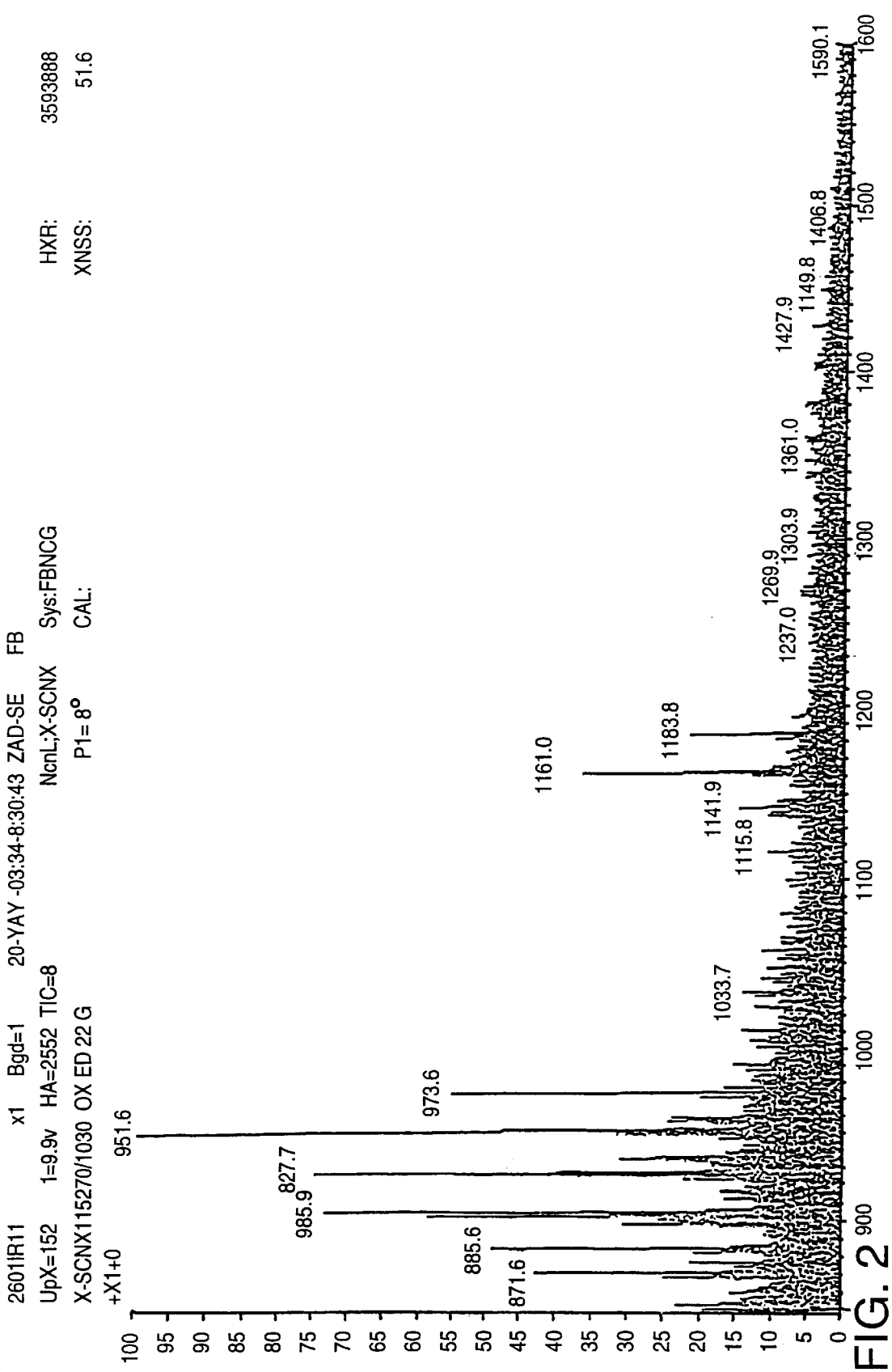

The FAB-MS spectrum of disaccharide B is given in FIG. 2 and shows a molecular peak at 1161.8 mass units (calculated 1161.3). The peak at 1183.8 mass units represents the addition of sodium. The peak at 951.6 represents the loss of a $C_{14}$ fatty acid. The peak at 973.6 mass units represents the fragment of the peak 951.6 with a sodium ion.

Figure 3:
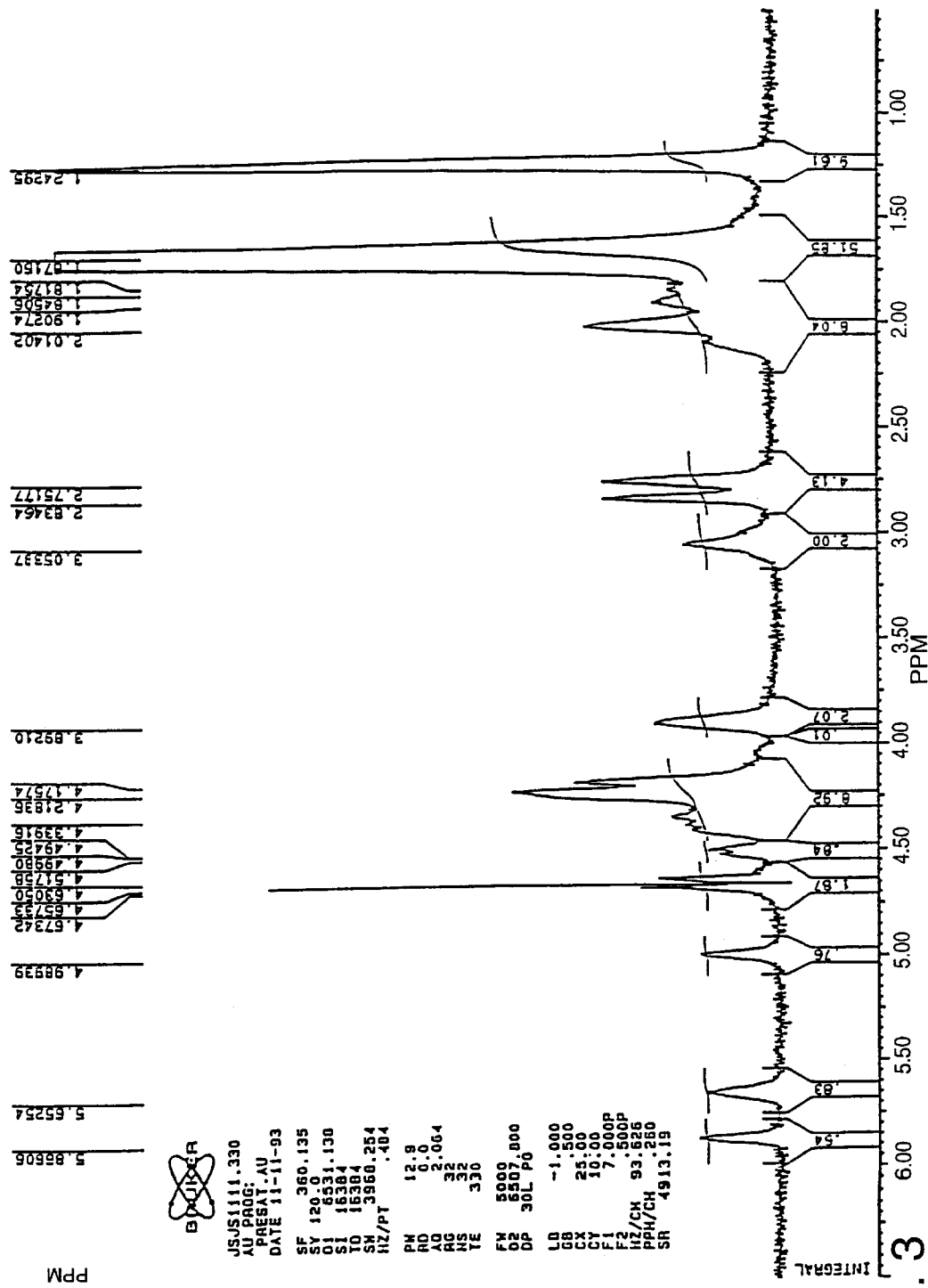
Figure 4:
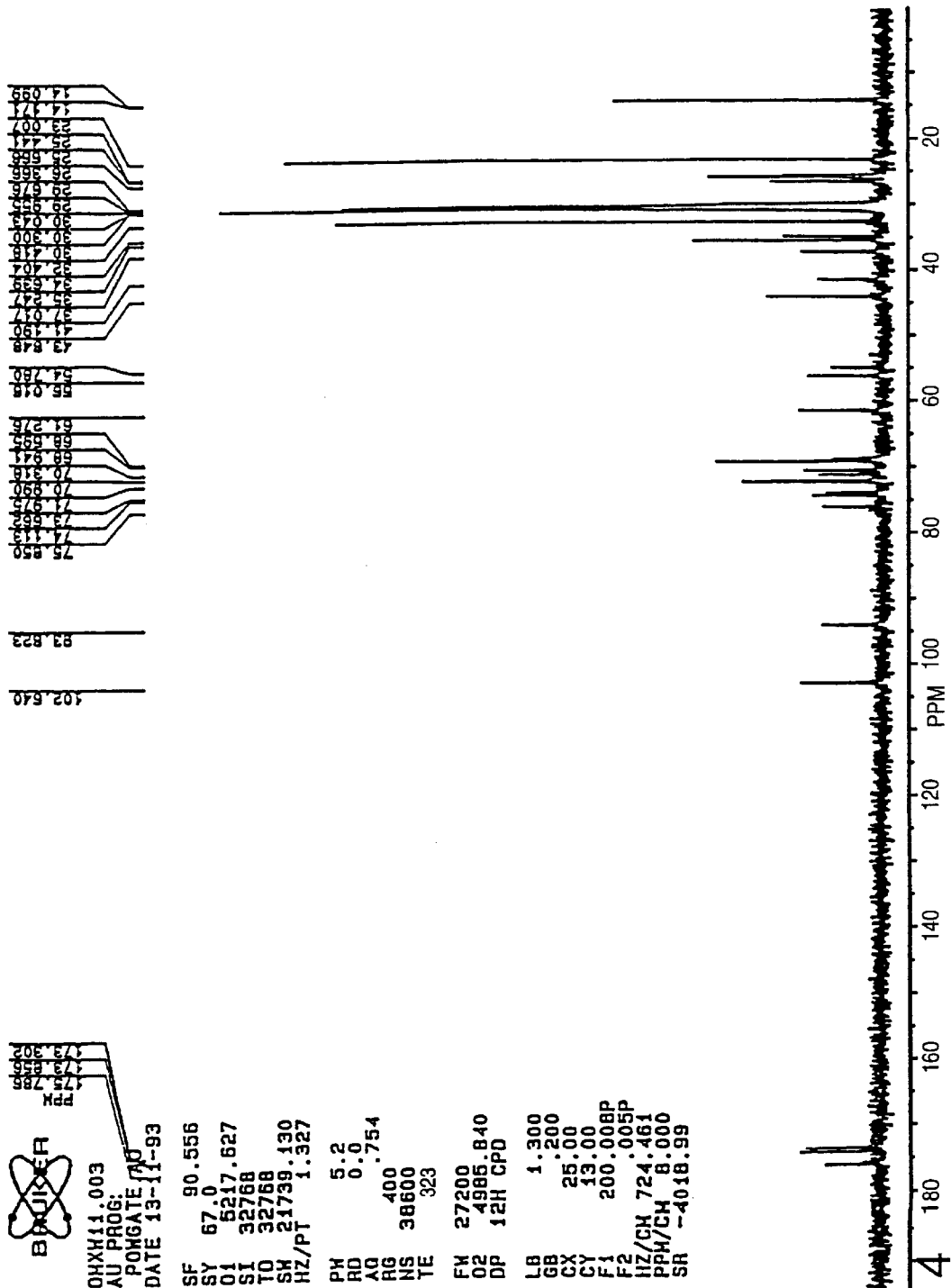
Figure 5:
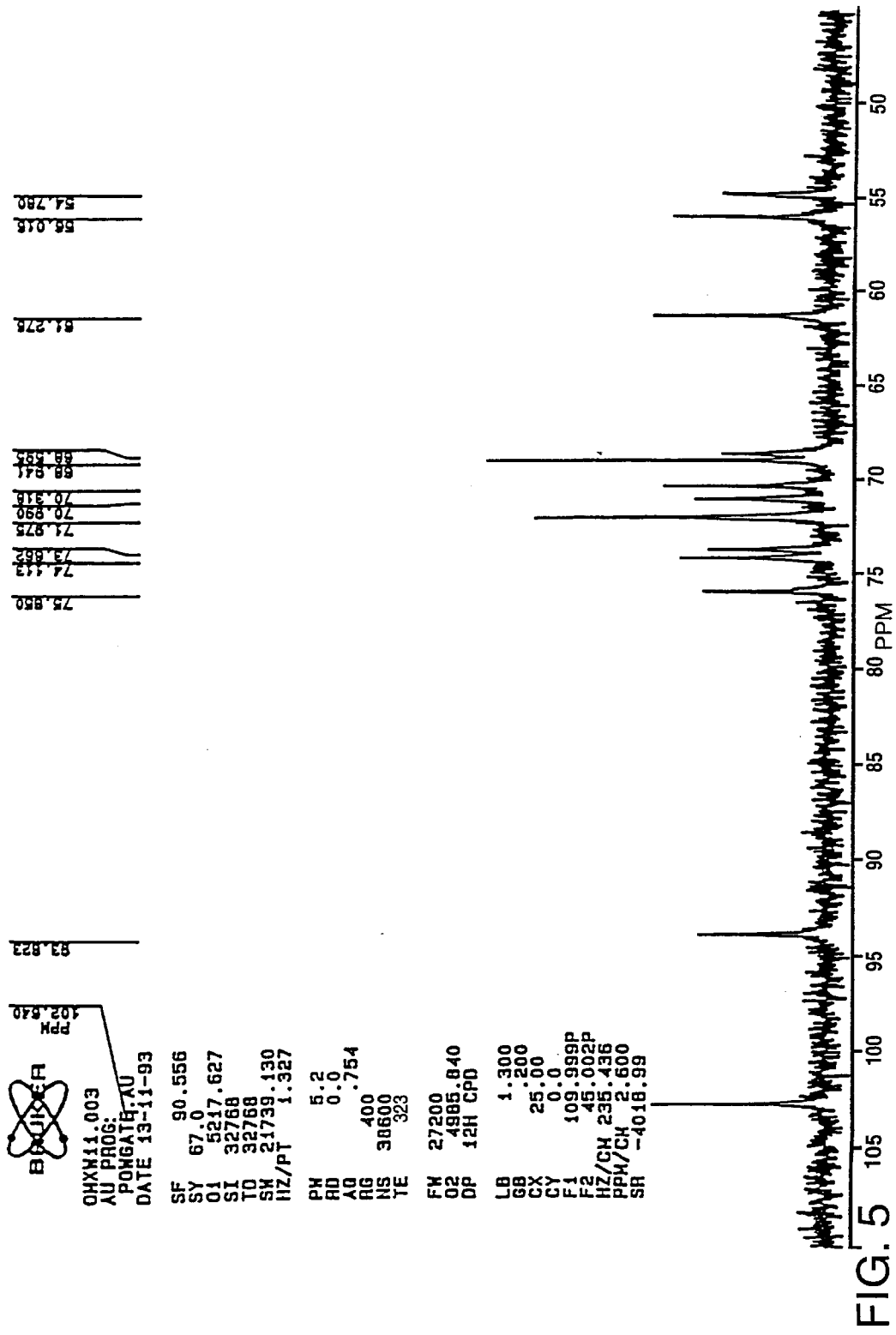

The $^1$H-NMR-spectrum (Bruker 360 MHz) of disaccharide A (sodium salt in $D_2O$) is given in FIG. 3 and its $^{13}$C-NMR-spectrum (Bruker 90 MHz) is given in FIGS. 4 and 5 (expanded scale).

The structural formula of the following β-D-glucosamine-(1–6)-α-D-glucosamine disaccharides:

disaccharide A (2-Deoxy-6-O-[2-deoxy-2-[(R)-3-dodecanoyloxytetradecanoylamino]-4-O-phosphono-β-D-glucopyranosyl]-2-[(R)-3-hydroxytetradecanoylamino]-α-D-glucopyranosyl dihydrogenphosphate);

disaccharide B (2-Deoxy-6-O-[2-deoxy-2-[(R)-3-tetradecanoyloxytetradecanoylamino]-4-O-phosphono-β-D-glucopyranosyl]-2-[(R)-3-hydroxytetradecanoylamino]-α-D-glucopyranosyl dihydrogenphosphate);

disaccharide C (2-Deoxy-6-O-[2-deoxy-2-[(R)-3-dodecanoyloxytetradecanoylamino]-4-O-phosphono-β-D-glucopyranosyl]-2-[(R)-3-dodecanoyloxytetradecanoylamino]-α-D-glucopyranosyl dihydrogenphosphate);

disaccharide D (2-Deoxy-6-O-[2-deoxy-2-[(R)-3-hydroxytetradecanoylamino]-4-O-phosphono-β-D-glucopyranosyl]-2-[(R)-3-dodecanoyloxytetradecanoylamino]-α-D-glucopyranosyl dihydrogenphosphate);

are disclosed hereafter.

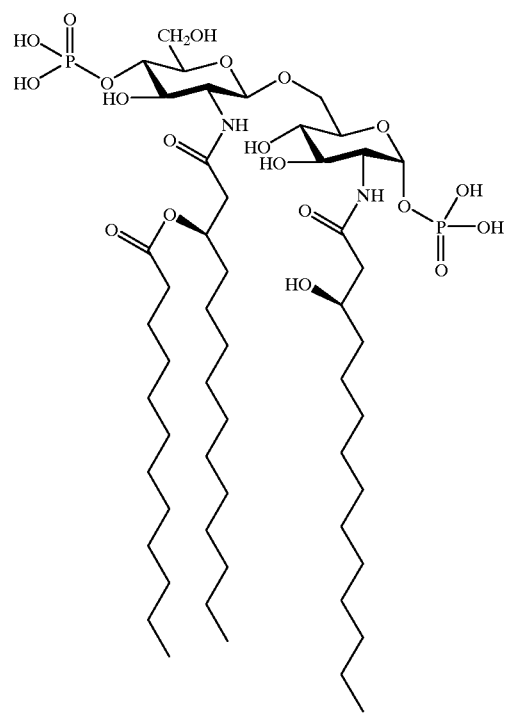

A

B

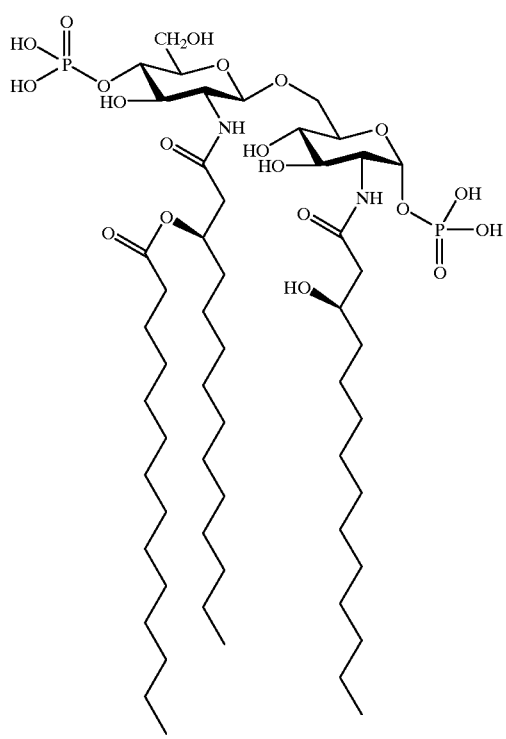

D

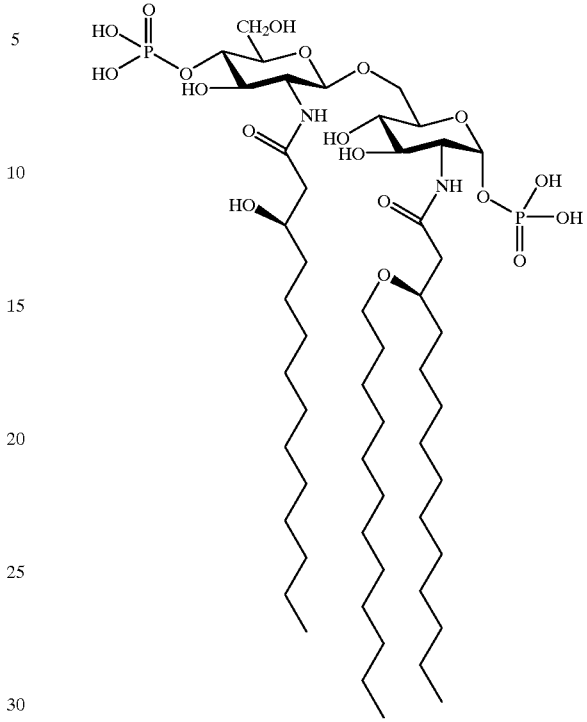

C

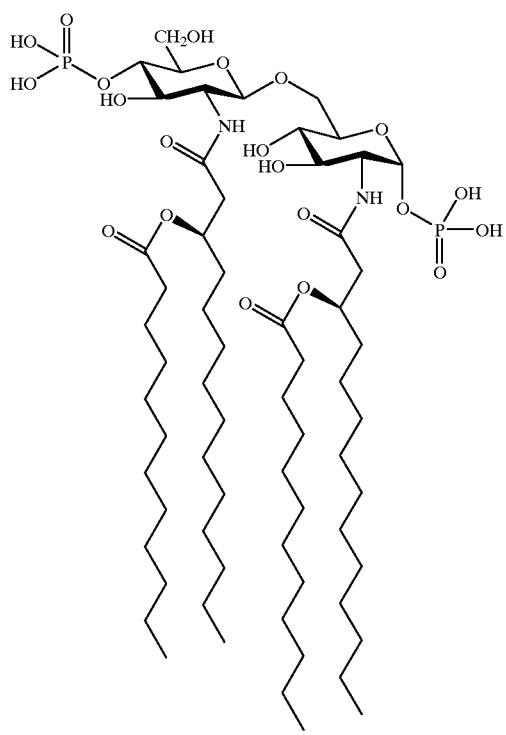

Endotoxicity and biological activity of disaccharides according to the invention The endotoxicity and the biological activity of disaccharide A (example 1) and of disaccharide B (example 2) were determined and compared to that of lipopolysaccharide originating from *Escherichia coli* O111:B$_4$ (Sigma, Product No. L3024), lipid A (Sigma, Product No. L5399; used as a starting material in example 4), and 3-O-deacylated lipid A originating from lipid A of *Escherichia coli* F583 (prepared as in the comparative example), but without purification by HPLC.

1. Endotoxicity

The endotoxicity was determined in the Limulus amoebocyte lysate (LAL) test. This test is based on the observation that endotoxins induce coagulation of the hemolymph of Limulus polyphemus.

In the gelification test serial dilutions of the compound to be tested were mixed with LAL 1:1, (v/v) (Haemachem Inc., sensitivity LAL 0.06 endotoxin units/ml), and the mixture was incubated for one hour at 37° C. Then gel formation was monitored by measuring the optical density at 405 nm. The last dilution which formed a gel was determined by inverting the reaction microplate. The endotoxin activity in the samples was determined by comparison with dilutions of a lipopolysaccharide standard (1 endotoxin unit=0.1 ng LPS).

The endotoxicity was also measured in the chromogenic test, in which the activation of a protease in LAL by LPS was measured using a chromogen (Ac-Ile-Glu-Ala-Arg-pNA;

Bio Whittaker Kit No. 50-650U). The colour formation (liberation of pNA (p-nitroaniline)) was measured at 405 nm.

Samples were pre-incubated at 37° C. during 10 minutes and subsequently chromogen-comprising LAL was added. The time required for reaching an optical density of 0.2 at 405 nm was measured. The endotoxin activity was calculated in comparison to a reference curve obtained for LPS standards.

The results are expressed in table 3 as: ng LPS per ng product.

TABLE 3

Endotoxic activity in LAL (ng/ng)

| Type of test | E. coli LPS[*1] | Lipid A | 3-O-deacylated lipid A | disaccharide A | disaccharide B | Monophosphoryl disaccharide A |
|---|---|---|---|---|---|---|
| Gelification | 0.9 ± 0.4 (n = 6) | 0.6 ± 0.3 (n = 3) | 1.0 ± 0.1 (n = 2) | 0.003 ± 0.002 (n = 12) | 0.004 ± 0.002 (n = 7) | 0.0031 ± 0.0013 (n = 10) |
| Chromogen | 0.70 (n = 1) | 0.7 ± 0.3 (n = 3) | 1.70 ± 0.95 (n = 3) | 0.0014 ± 0.0013 (n = 9) | 0.0008 ± 0.0006 (n = 7) | 0.0016 ± 0.0009 (n = 10) |

[*1]Endotoxic activity of LPS in LAL = 1 ng/ng, experimental data are within the range of 0.3–3 ng/ng.

Thus table 3 shows that disaccharides A and B according to the invention exhibit the lowest endotoxicity, in particular with regard to 3-O-deacylated lipid A according to U.S. Pat. No. 4,912,094.

2. In vitro biological activity induced in macrophages of C57BL/6 mice

Bone marrow was collected from hip, femur and tibia of six week old male C57BL/6 mice. After homogenization of the marrow suspension in Dulbecco modified medium and centrifugation, the pellet was resuspended in Dulbecco modified medium and the cells were cultivated at a concentration of $4 \times 10^5$ cells per ml in the same medium supplemented with 30% supernatant of L-929 fibroblasts (a common source for colony stimulating factor 1 [CSF-1]) and 20% horse serum.

After 7 days the mature macrophages were collected and resuspended in Dulbecco modified medium comprising 5% foetal calf serum to a concentration of $7 \times 10^6$ cells per ml. This cell suspension was mixed 1:1, (v/v) with samples diluted in the same medium and used in the biological tests performed in microplates with 70,000 cells/well (incubation at 37° C. for 22 hours, 100% humidity and 8% $CO_2$).

Nitric oxide (NO) production

Nitric oxide (NO) is produced by macrophages in response to bacterial infection and in particular LPS. NO seems to have cytostatic and cytotoxic properties. NO is extremely reactive and rapidly converted by oxidation into nitrite and nitrate.

The nitrite formation was determined using the Griess test (addition of 1:1, (v/v) N-(1-naphthyl)ethylene diamine hydrochloride [1 g/l in water] and p-aminobenzenesulphonamide [10 g/l in 5% $H_3PO_4$]). The nitrite concentration in supernatants of activated macrophages was calculated in comparison to $NaNO_2$ standards.

The results are disclosed in table 4.

TABLE 4

NO-production in the supernatants of macrophages stimulated by LPS and derived products

| Product | Maximum activity[*)] | Minimum activity[*)] | Activity 50%[*)] | NO activity at 50% in nmol $NO_2^-$/ml[**)] | Number of analyses |
|---|---|---|---|---|---|
| LPS E. Coli | 100 | 0.0004 | 0.01 | 7 | n = 6 |
| Lipid A | 50 | 0.005 | 0.07 | 5 | n = 7 |
| 3-O-deacylated lipid A | 50 | 0.005 | 0.16 | 5 | n = 3 |
| Disaccharide A | 50 | 0.016 | 0.16 | 5 | n = 6 |
| Disaccharide B | 16 | 0.0005 | 0.05 | 5 | n = 1 |
| Monophosphoryl disaccharide A | 50 | 5 | 8 | 4 | n = 1 |

[*)]Product concentration expressed as µg/ml, corresponding to induced NO activity.
[**)]Concentration in $NO_2^-$/ml extrapolated from the series dilution curve.

LPS induces the highest NO production. Lipid A, 3-O-deacylated lipid A, disaccharide A and disaccharide B induce NO production of the same order.

Thus disaccharides A and B induce NO-production in macrophages as strongly as lipid A and 3-O-deacylated lipid A.

Production of interleukin-1α (IL-1α)

IL-1α is produced by a number of cells including macrophages when stimulated by LPS. Some reported IL-1α activities include the activation of T-cells, induction of Il-2 receptor expression and cytokine gene expression in T-cells, co-stimulation of B-cell-proliferation and Ig secretion, and augmentation of Il-2 and IFN-induced activation of NK-mediated cytotoxicity, induction of acute phase protein synthesis and fever induction.

The concentration of IL-1α in the supernatants of macrophages was measured by an ELISA-test (Kit GENZYME, Intertest-1α).

The results are summarized in table 5.

TABLE 5

Production of IL-1α in the supernatants of macrophages stimulated by LPS and derived products

| Product | Highest concentration tested | | Concentration 500 µg/ml IL-1α [pg/ml] | Minimum activity detected | |
|---|---|---|---|---|---|
| | concentration [µg/ml] | IL-1α [pg/ml] | | concentration [µg/ml] | IL-1α [pg/ml] |
| Blank = TEA 0.1% | 500 | <15*) | <15*) | | <15*) |
| LPS E. coli | 1600 | 295 ± 129 | 170**) | 1.56 | 18 ± 4 |
| Lipid A | 500 | 53 ± 35 | 53 ± 35 | 50 | 17 ± 8 |
| 3-O-deacylated lipid A | 500 | 56 ± 19 | 56 ± 19 | 160 | 21 ± 6 |
| Disaccharide A | 500 | 75 ± 45 | 75 ± 45 | 16 | 19 ± 11 |

*)The limit of test detection is in the order of 15 pg/ml.
**)IL-1α concentration extrapolated from the series dilution curve.

It was not possible to determine the maximum production of IL-1α, because the production was still increasing at the highest concentration used.

The induction of IL-1α production at a concentration of 500 µg/ml is not significantly different for lipid A, 3-O-deacylated lipid A and disaccharide A. LPS induces IL-1α production more strongly.

The IL-1α production by disaccharide A is at least as strong as by lipid A and 3-O-deacylated lipid A.

Production of interleukin-6 (IL-6)

IL-6 is produced by activated monocytes or macrophages, T- and B-lymphocytes. IL-6 induces among others proliferation of certain types of cells, growth inhibition of certain melanoma cell lines, differentiation of B-lymphocytes and stimulation of IgG secretion, differentiation of cytotoxic T-cells, and a weak anti-viral activity.

IL-6 concentration in supernatants of macrophages was determined by an ELISA test (Kit ENDOGEN, EM-IL-6).

The results are summarized in table 6.

TNF-α is mainly produced by macrophages and monocytes stimulated by LPS. The activities induced by TNF-α are inter alia an anti-viral activity, cytolysis and cytostasis of certain cell types, growth of certain cellular lines, antigen expression such as major histocompatibility complexes class I and II, necrosis of methylcholanthrene-induced sarcoma, and II, necrosis of methylcholanthrene-induced sarcoma, activation of polymorphonuclear leukocytes (PMN), osteoclast activation and bone resorption. TNF-α is also a principal mediator in toxic shock and sepsis.

The concentration of TNF-α in supernatants of macrophages was determined by an ELISA test (Kit GENZYME, Factor-test mTNF-α).

The results are listed in table 7.

TABLE 7

Production of TNF-α in the supernatants of macrophages by LPS and derived products

| Product | Highest concentration tested | | Concentration 500 µg/ml TNF-α [pg/ml] | Minimum activity detected | |
|---|---|---|---|---|---|
| | concentration [µg/ml] | TNF-α [pg/ml] | | concentration [µg/ml] | TNF α [pg/ml] |
| Blank = TEA 0.1% | 500 | 138 ± 9 | 138 ± 9 | 0 | <100*) |
| LPS E. coli | 100 to 6.25 | 257 to 284 | 130***) | 0.006 | 175 ± 55 |
| Lipid A | 500 | 223 ± 64 | 223 ± 64 | 0.016 | 118 ± 9 |
| 3-O-deacylated lipid A | 500 | 311 ± 72 | 311 ± 72 | 0.016 | 155 ± 6 |
| Disaccharide A | 500 | 530 ± 139 | 530 ± 139 | 0.16 | 159 ± 43 |

*)The limit of test detection is in the order of 100 pg/ml.
**)TNF-α concentration is relatively constant between 100 and 6.25 µg/ml of LPS, and decreases for concentrations greater than 200 µg/ml.
***)TNF-α concentration is extrapolated from the series dilution curve.

It was not possible to determine the maximum production of TNF-α, because the production was still increasing at the highest concentration tested.

TABLE 6

Production of IL-6 in the supernatants of macrophages stimulated by LPS and derived products

| Product | Maximum activity | | Minimum activity | | 50% activity | |
|---|---|---|---|---|---|---|
| | concentration [µg/ml] | IL-6 [pg/ml] | concentration [µg/ml] | IL-6 [pg/ml] | concentration [µg/ml] | IL-6 [pg/ml] |
| Blank = TEA 0.1% | 500 | 1150 ± 80 | 0 | 710 ± 240 | — | — |
| LPS E. coli | 25 | 13860 ± 2750 | 0.006 | 2400 ± 960 | 0.3 | 6950 |
| Lipid A | 160 to 0.016*) | 3000 to 2200*) | 0.015 | 2460 ± 50 | ND**) | ND**) |
| 3-O-deacylated lipid A | 160 to 0.016*) | 2850 to 2200*) | 0.016 | 2410 ± 160 | ND**) | ND**) |
| Disaccharide A | 50 | 5700 ± 2650 | 0.016 | 850 ± 350 | 1 | 2850 |

*)The induced activity is relatively constant within the tested range and does not give a maximum.
**)ND = not determined.
The activity induced by the weakest concentration of tested product (0.016) is still greater than the 50% activity.

The stimulation of IL-6 secretion by disaccharide A is significantly lower than for LPS. However, disaccharide A induces IL-6 production in macrophages more strongly than lipid A and 3-O-deacylated lipid A.

Production of tumor-necrosis-factor-alpha (TNF-α)

In contrast to the other tests, the TNF-α production induced by LPS was lower than for disaccharide A. Disaccharide A induced TNF-α equally or more strongly than lipid A or 3-O-deacylated lipid A.

Prostaglandin E2 (PGE2) production

PGE1 and PGE2 are the main metabolites of arachidonic acid synthesized by macrophages stimulated by LPS, TNF-α, or IL-1. PGE's exhibit immunomodulating activities on T- and B-lymphocytes. They seem to induce a stimulation of the Th2 and an inhibition of Th1 T-lymphocyte subpopulations and a switch in the isotype of immunoglobulines.

The PGE2 concentration in the supernatants of macrophages was measured by a RIA-test (Kit PAESEL+LOREI, 36-104-6001 Prostaglandin E2 3H-RIA Kit).

The results are summarized in table 8.

TABLE 8

Production of PGE2 in the supernatants of macrophages stimulated by LPS and derived products

| Product | Highest concentration inducing an activity | | Lowest concentration inducing an activity | |
|---|---|---|---|---|
| | concentration [µg/ml] | PGE2 [pg/ml] | concentration [µg/ml] | PGE2 [pg/ml] |
| Blank = TEA 0.1% | 500 | <80*) | — | <80*) |
| LPS E. coli | 1600 | 1120 ± 135 | 6.25 | 153 ± 29 |
| Lipid A | 500 | <80*) | — | <80*) |
| 3-O-deacylated lipid A | 500 | 240 ± 25 | 500 | 240 ± 25 |
| Disaccharide A | 500 | 540 ± 65 | 16 | 80 ± 41 |

*)The test detection limit is of the order of 80 pg/ml.

It was not possible to determine the maximum production of PGE2, because the production was still increasing at the highest concentration used. The stimulation of PGE2 production by disaccharide A is significantly lower than for LPS. However, disaccharide A was more active than lipid A and 3-O-deacylated lipid A. Lipid A did not induce PGE2 production and 3-O-deacylated lipid A only at the highest concentration used.

Conclusion greater activity is the LPS which induced generally a higher response and required a lower concentration to induce a significant signal.

3. In vivo biological activity

The in vivo biological activity of disaccharide A was investigated for anti-tumor activity against peritoneal carcinomatosis induced in BDIX rats. Pro b cells obtained according to the method of Martin (Martin, F. et al, International Journal of Cancer, Volume 32, pages 623–627 [1983]) were injected intraperitoneally in rat ($10^6$ cells per rat). After 10 days numerous solid nodules appear in the mesenterium in the milky spots and progressively invade the peritoneal cavity (see Lagadec, P. et al, Invasion and Metastasis, Volume 7, pages 83–95 [1987]). Hemorrhagic ascitis appeared after 4–5 weeks and all rats died within 8–12 weeks.

Immunotherapy started 14 days after injection of the tumoral Pro b cells. The treatment consisted of intraperitoneal injections of disaccharide A; doses 0.1, 0.3 and 0.8 mg/kg bodyweight. Disaccharide A was dissolved in an aqueous solution of 0.9% NaCl and 0.1% triethylamine. The rats received five injections once every 3.5 days. A control group was injected with the aqueous solution. Both groups comprised 10 rats.

6 Weeks after the injection of the tumoral cells autopsy was carried out. The extent of peritoneal carcinomatosis was evaluated blindly and the rats were classified in the order of increasing carcinomatosis.

The classification of the nodule size is as follows:

class 0: no tumor nodules visible;
class 1: a few nodules of size less than 0.2 cm;
class 2: nodules too many to be counted size up to 0.5 cm;
class 3: tumors in size up to 1 cm;
class 4: tumoral cavity entirely invaded by tumors, size a few cm.

The results are reviewed in table 9.

TABLE 9

In vivo anti-tumoral activity of disaccharide A in peritoneal carcinomatosis

| Disaccharide A | Number of rats with carcinomatoses of class: | | | | | Effect of product | Ascitis volume [ml/rat] | | Effect of product |
|---|---|---|---|---|---|---|---|---|---|
| (dose) | 0 | 1 | 2 | 3 | 4 | (1) | Limits | Average | (2) |
| 0 mg/kg | 0 | 1 | 1 | 2 | 6 | | 0–64 | 40 ± 24 | |
| 0.1 mg/kg | 0 | 2 | 0 | 4 | 4 | NS | 0–18 | 7 ± 7 | p < 0.001 |
| 0.3 mg/kg | 2 | 3 | 2 | 2 | 1 | p < 0.01 | 0–20 | 2 ± 6 | p < 0.001 |
| 0.8 mg/kg | 1 | 6 | 1 | 1 | 1 | p < 0.01 | 0–2 | 0 ± 1 | p < 0.001 |

The disaccharides according to the invention are active in vitro and induce the production of NO, IL-1α, IL-6, TNF-α and PGE2. The disaccharides according to the invention are as active, or even more active, than lipid A and 3-O-deacylated lipid A, but exhibit a substantially reduced endotoxicity as determined by the LAL test. The lower activity of lipid A and 3-O-deacylated lipid A could be due to differences in purity. Disaccharides A and B are purified by HPLC, lipid A is a commercial biological preparation (Sigma L-5399) and 3-O-deacylated lipid A is prepared according to U.S. Pat. No. 4,912,054 starting from the commercial preparation of lipid A. The only product with The statistical significance of the anti-tumoral activity was calculated by the Kruskal-Wallis test (1) or (2) using variance analysis.

Obviously, disaccharide A possesses a dose-dependent anti-tumoral effect.

4. Acute toxicity

Disaccharide A was injected into the caudal vein of male and female NMRI mice (age 6–7 weeks). A dose up of 100 mg/kg bodyweight did not induce any death.

EXAMPLE 7

The starting material is lipopolysaccharide from *Pseudomonas aeruginosa* (Sigma, Product No. L7018). The structure of lipid A is already known (see Kulshin et al. in Eur. J. Biochem. 198 (1991) 697–704). In contrast to lipid A from *E. coli*, the predominant species contain acyloxyacyl residues at both amino groups of the diglucosamine diphosphate backbone. In addition there is a 3-hydroxydecanoic acid at position 3', but the same fatty-acyl residue is only present at position 3 in a minor fraction.

Removal of this fatty-acyl residue at position 3' would lead to an analogue of disaccharide C. Further hydrolysis would lead to loss of the esterified fatty-acyl residue at the acyloxyacyl group at either the position 2 or 2'. These structures are analogues to the disaccharides C and D.

Lipopolysaccharide from *Ps. aeruginosa* (Sigma L7018) was dissolved in 0.1 M sodium acatate pH 4.0 at 5 mg/ml and heated for 120 min. at 100° C. After cooling, 0.5 volumes of propan-2-ol were added followed by tetrabutylammonium phosphate (TBAP) to 25 mM final concentration. Triethylamine (TEA) was added to pH 9.0 (approx., pH papers). The mixture was applied to a C18 Sep-Pak (Waters) with recycling (10 passages). The Sep-Pak was washed with 10 ml 5 mM TBAP in acetonitrile:H$_2$O 1:1 (v/v) followed by 10 ml acetonitrile. The adsobed substances were eluted with 4 ml chloroform:methanol 2:1 (v/v).

The two major peaks, PsA1 and PsA2 (FIG. 6) were purified by HPLC and the fatty acids analysed. The fatty acid composition corresponds to the molecules described by Kulshin et al. (table below). PsA1 is less hydrophobic than PsA2 as it elutes from the column with a lower retention time (R$_t$). This corresponds to the molecule with two 2OH-C12:0 acid residues. PsA2 has both 2OH-C12:0 and C12:0.

| Peak | Fatty acid identified |
|---|---|
| PsA1 | 3OH-C10:0 |
|  | 2OH-C12:0 |
|  | 3OH-C12:0 |
| PsA2 | 3OH-C10:0 |
|  | C12:0 |
|  | 2OH-C12:0 |
|  | 3OH-C12:0 |

The solvent was removed by rotary evaporation and the residue redissolved in 0.2%. TEA in water.

Sodium hydroxide was added to the solution of *Ps. aeruginosa* lipid A to a concentration of 0.2 M and the solution was incubated at room temperature for 60 min. The solution was then neutralized with (8.5%) orthophosphoric acid. It was then applied to a reversed-phase HPLC system (HP1050 with a Supelco LC18, 3 μm reversed-phase column, with precolumn) equilibrated in 75% solvent A (5 mM TBAP in acetronile water 1:1 (v/v) 25% solvent B (5 mM TBAP in propan-2-ol:water 9:1 (v/v)) and eluted with a gradient of 2% solvent B/min to 100% B. Peaks were detected by absorption at 210 nm. The major peaks were collected (see FIG. 7). These were diluted with 2 volumes water and applied to C18 Sep-Pak cartridges equilibrated in solvent A. The Sep-Pak's were washed with 10 ml 0.45% sodium chloride in propan-2-ol:H$_2$O 1:3 (v/v), 10 ml water and 10 ml acetonitrile. The adsorbed substances were eluted with 4 ml chloroform:methanol 2:1 (v/v) and the solvents removed under nitrogen. The fractions were redissolved in 100 μl water.

The fatty-acyl content of the fractions was analysed by gas chromatography after hydrolysis in 4 M HCl, 100° C., 4 h. The released fatty acids were converted to the methyl esters according to Miller (Miller, L. Gas Chromatography application note 228-37 [Hewlett Packard]) and analysed on a Hewlett-Packard 5890 gas chromatogram with a fused silica column (Supelco 2-4026) with reference to standard fatty acid methyl esters (Supelco).

After hydrolysis of the lipid A extract, many peaks are observed on reversed-phase HPLC. The main peaks (PsAOH1, 2, 4 and 6) were collected from the HPLC. The fatty-acids identified in each fraction are shown below.

| Peak | Fatty acid identified |
|---|---|
| PsAOH1 | 3OH-C12:0 |
|  | 2OH-C12:0 |
| PsAOH2 | 3OH-C12:0 |
|  | 2OH-C12:0 |
| PsAOH4 | 3OH-C12:0 |
|  | C12:0 |
| PsAOH6 | 3OH-C12:0 |
|  | 2OH-C12:0 |
|  | C12:0 |

The structural formula of these disaccharides are as follows:

PsAOH1: 2-Deoxy-6-O-[2-deoxy-2-[(R)-3-[(S)-2-hydroxydodecanoyloxy]-dodecanoylamino]-4-O-phosphono-β-D-glucopyranosyl]-2-[(R)-3-hydroxydodecanoylamino]-α-D-glucopyranosyl dihydrogenphosphate;

PsAOH2: 2-Deoxy-6-O-[2-deoxy-2-[(R)-3-hydroxydodecanoylamino]-4-O-phosphono-β-D-glucopyranosyl]-2-[(R)-3-[(S)-2-hydroxydodecanoyloxy]-dodecanoylamino]-α-D-glucopyranosyl dihydrogenphosphate;

PsAOH4: 2-Deoxy-6-O-[2-deoxy-2-[(R)-3-dodecanoyloxydodecanoylamino]-4-O-phosphono-β-D-glucopyranosyl]-2-[(R)-3-hydroxydodecanoylamino]-α-D-glucopyranosyl dihydrogenphosphate;

PsAOH6: 2-Deoxy-6-O-[2-deoxy-2-[(R)-3-dodecanoyloxydodecanoylamino]-4-O-phosphono-β-D-glucopyranosyl]-2-[(R)-3-[(S)-2-hydroxydodecanoyloxy]-dodecanoylamino]-α-D-glucopyranosyl dihydrogenphosphate;

are disclosed hereafter.

disaccharide E (PsAOH1)
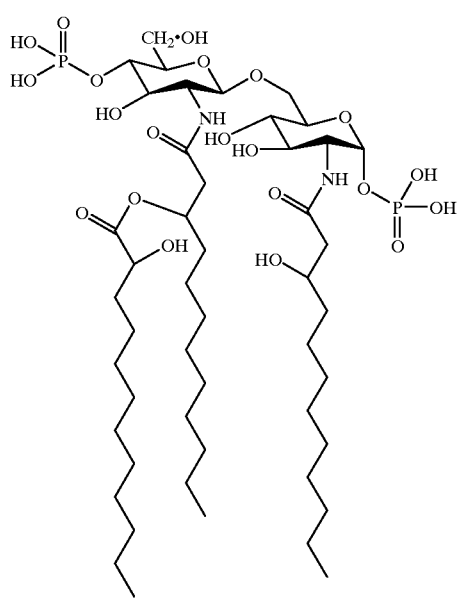
disaccharide F (PsAOH2)
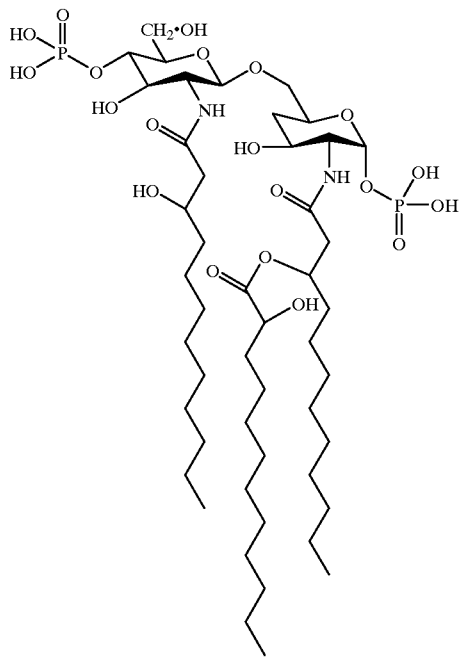
disaccharide G (PsAHO4)
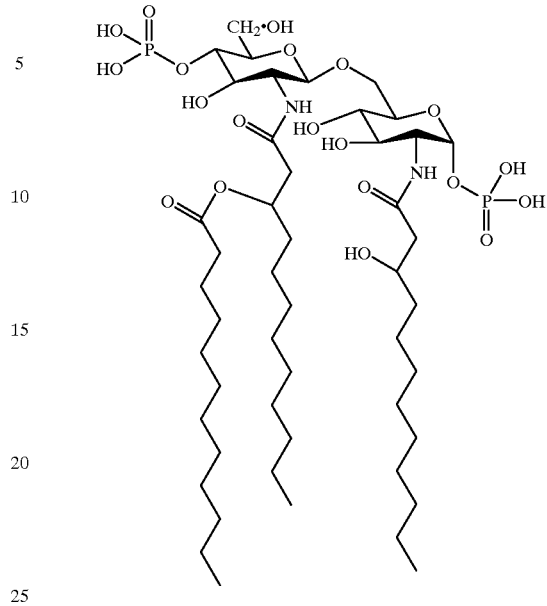
disaccharide H (PSAOH6)
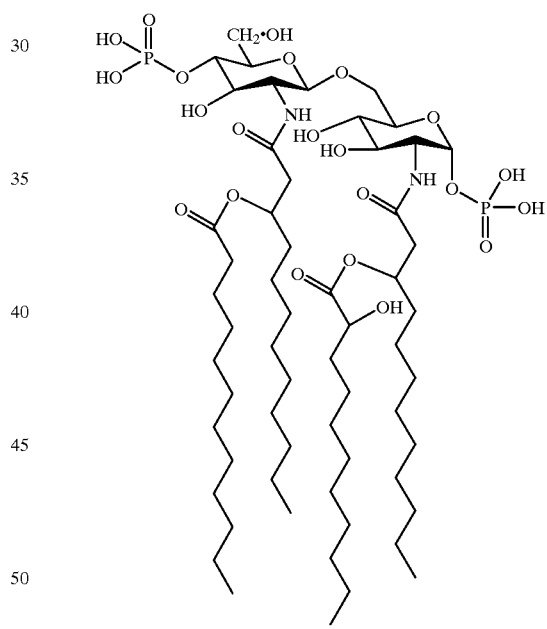
The fractions were also analysed by electro-spray mass spectrometry (ES-MS) in the negative mode. A VG Biotech BIO-Q instrument was used with a triple quadrupole analyser. 2 to 4 µl of each sample was diluted into 10 µl acetonitrile:water:25% ammonia solution, 50:50:1 (v/v). 10 μl were then injected directly into the source of the mass spectrometer. Acetonitrile:water:25% ammonia solution, 50:50:1 (v/v) at 7 μl/min was used as eluant. For analysis of the fragmentation of the principle ions, parent ions from the first quadrupole were subjected to collision activated decomposition in the second quadrupole using argon as the collision gas. Daughter ions were detected in the third quadrupole.

The mass calculated for each of the peaks and the mass observed by ES-MS are given below.

| Peak | Calculated mass | Observed mass |
|------|-----------------|---------------|
| PsAOH1 | 1093.5 | 1093.4 |
| PsAOH1 | 1093.5 | 1093.1 |
| PsAOH4 | 1077.5 | 1077.0 |
| PsAOH6 | 1275.8 | 1275.7 |

There is a very good correspondence in each case.

In the case of PsAOH1 and PsAOH2 the masses are identical. This indicates that they represent two isoforms of the molecule, Lipid A's are known to fragment under certain analytical conditions in mass spectrometry (Kulshin, 1991; and Cotter et al., Biomed. Encl. Mass Spectrom. 14 (1987), 591–598). Ions are produced which represent the non-reducing half of the molecule with an addition of 102 mass units. Thus with two MS in tandem the principle ion in the first MS can be fragmented and the "daughter" ions detected in the second MS. This eliminates the possibility that the secondary ions observed are contaminants; they must come from the original ion by fragmentation. The mass of the daughter ions expected for each fraction and the masses observed on MS-MS are shown hereafter.

| Peak | Calculated mass of fragment | Observed mass of fragment |
|------|-----------------------------|---------------------------|
| PsAOH1 | 558.5 or 756.8 | 756.1 |
| PsAOH2 | 558.5 or 756.8 | 557.7 |
| PsAOH4 | 558.5 or 740.8 | 739.9 |
| PsAOH6 | 558.5 or 740.8 | 740.1 |

These observations clearly identify the structures of the disaccharides E, F, G, and H.

For internal comparison disaccharide A was also analysed by ES-MS. The calculated mass was 768.9 and the observed mass of fragment 768.

The biological activity of the fractions was tested by the stimulation of nitrite production in murine peritoneal macrophages as described hereinbefore.

Figure 8:
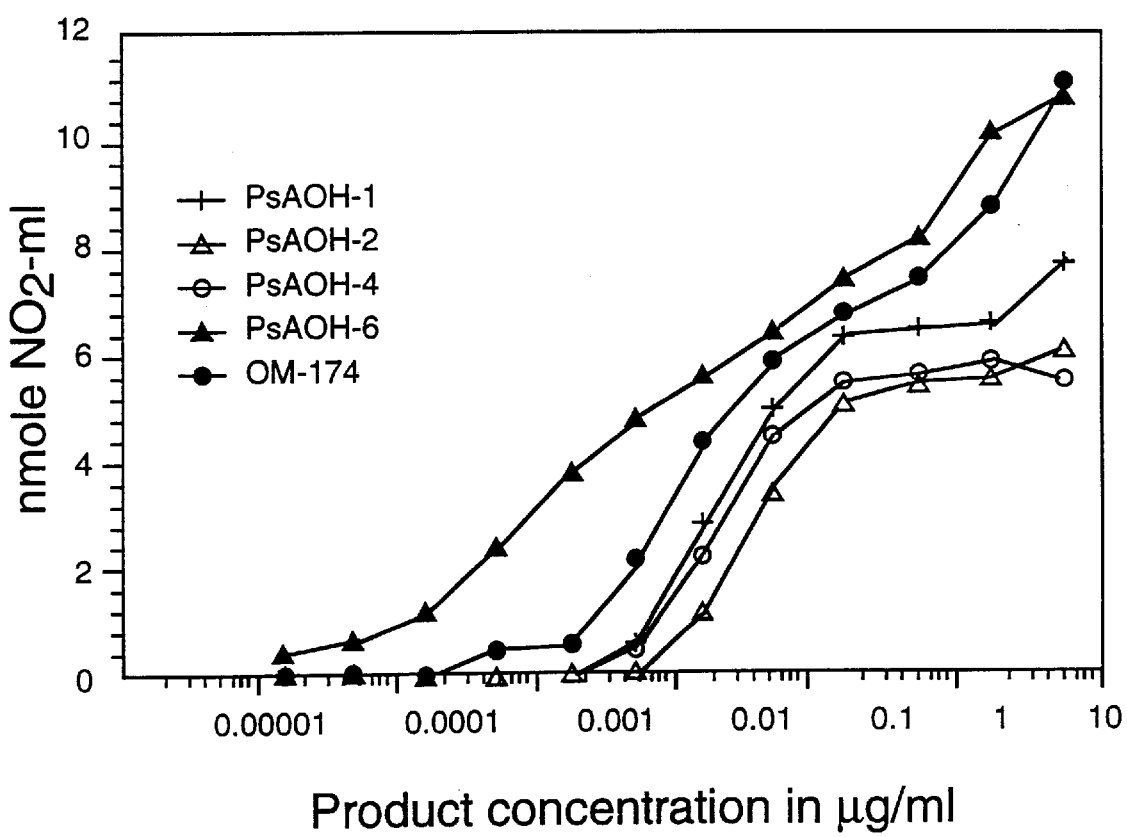

The quantity of each analogue in the stock solution was determined from the absorption on HPLC with reference to that of disaccharide A. The fractions show activities of the same order as disaccharide A (FIG. 8). Disaccharide H, which has two acyloxyacyl groups and no other fatty-acyl residues, is the most active. The position of the acyloxyacyl, 2 versus 2', has only a minor influence on the activity.

In order to eliminate the possibility that activity was due to contamination of the samples by other substances such as LPS, disaccharides E, F, G and H were repurified on reversed-phase HPLC and the regions of the HPLC baseline just before and just after the peak were also collected and treated in the same way as the fractions containing the peaks of material. The activity of the peak fractions and the baseline fractions was tested. The peaks containing disaccharide E, F, G and H showed similar activity to that seen in the first assay. The blank samples, representing the regions of the HPLC profile just before and after the peak of lipid A analogue, were inactive. The stimulation of nitrite production is thus specifically associated with the lipid A analogues.

The endotoxicity of the disaccharides E, F and G was determined using the chromogenic LAL test (see infra). However, instead of using 1 mg/ml bovine serum albumin, 0.1 mg/ml has been used. The results (n=4 or 6) were obtained in two series of experiments and are shown hereafter.

| Sample | Endotoxic activity in LAL (mg/mg) |
|--------|-----------------------------------|
| E. coli LPS | 0.58 ± 0.14 |
| E. coli lipid A | 0.32 ± 0.06 |
| disaccharide E | 0.000005 ± 0.000002 |
| disaccharide F | 0.000025 ± 0.000026 |
| disaccharide G | 0.00006 ± 0.00003 |
| disaccharide A | 0.000003 ± 0.000002 |

We claim:

1. A β(1→6) glucosamine disaccharide having reduced endotoxicity, said disaccharide having the formula

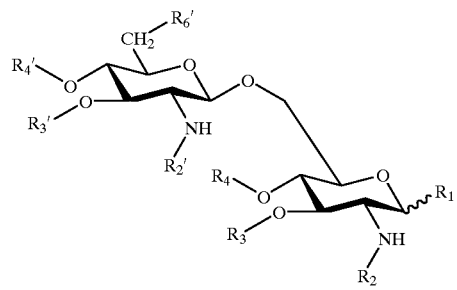

wherein
$R_1$ is a hydroxyl group,
   a dihydroxyphosphonoyloxy group or its charged forms,
   a $(C_1–C_5)$ acyloxy group,
   a $(C_1–C_5)$ alkyloxy group, or
   a group X;
$R_2$ and $R_2'$ are each an acyl group or a group Y, with at least one of $R_2$ and $R_2'$ being the group Y;
$R_3$ and $R_3'$ are each hydrogen,
   a $(C_1–C_3)$ alkyl group, or
   a $(C_1–C_3)$ acyl group;
$R_4$ is hydrogen,
   a $(C_1–C_3)$ alkyl group; or
   a $(C_1–C_3)$ acyl group;
$R_4'$ is hydrogen,
   a $(C_1–C_5)$ acyl group,
   a $(C_1–C_5)$ alkyl group, or
   a dimethoxyphosphonoyl group, or
   a phosphono group or its charged forms; and
$R_6'$ is hydrogen,
   a hydroxyl group,
   a dihydroxyphosphonoyloxy group, a hydroxysulphonyloxy group, their charged forms,
or a group Z;
wherein the group X is selected from the group consisting of
 a carboxy ($C_1$–$C_5$) alkyloxy group;
 an —O—CH—[$(CH_2)_m$COOH][$(CH_2)_n$COOH] group, wherein
  m=0–5 and
  n=0–5;
 a phosphono ($C_1$–$C_5$) alkyl group;
 a dimethoxyphosphonoyloxy group;
 a hydroxysulphonyloxy group;
 a hydroxysulphonyl ($C_1$–$C_5$) alkyl group; and
 charged forms of the group X;
wherein the group Y is a branched acyl group selected from the group consisting of
 an acyloxyacyl group,
 an acylaminoacyl group,
 an acylthioacyl group,
 a ($C_1$–$C_{24}$) alkyloxyacyl group,
 a ($C_1$–$C_{24}$) alkylaminoacyl group, and
 a ($C_1$–$C_{24}$) alkylthioacyl group; and
wherein the group Z is selected from the group consisting of
 a ($C_1$–$C_{24}$) alkyloxy group;
 a ($C_1$–$C_{24}$) acyloxy group;
 3-deoxy-D-manno-2-octulosonic acid (KDO);
 (KDO)$_n$, wherein n=1–10;
 a polysaccharide side chain; a core component; and
 an amino-($C_1$–$C_8$) alkyl-carboxyl group;
and its salts.

2. Disaccharide according to claim 1, wherein the group Y is selected from the group consisting of a 3-acyloxyacyl group, a 3-acylaminoacyl group, and a 3-acylthioacyl group.

3. Disaccharide according to claim 1, wherein the group Y is an acyloxyacyl group.

4. Disaccharide according to claim 1, wherein the acyl group is selected from the group consisting of a fatty acid residue, a 3-hydroxy fatty acid residue, and a 3-oxo fatty acid residue.

5. Disaccharide according to claim 1, wherein the acyloxyacyl group, the acylaminoacyl group and the acylthioacyl group forming the group Y, comprise acyl moieties selected from the group consisting of a fatty acid residue, a 3-hydroxy fatty acid residue, and a 3-oxo fatty acid residue.

6. Disaccharide according to claim 5, wherein the group Y is an acyloxyacyl group which is an N-linked 3-hydroxy ($C_4$–$C_{24}$)-acyl [, preferably ($C_8$–$C_{18}$)-fatty acid-acyl] ester-linked at the 3-hydroxy position with a ($C_1$–$C_{20}$)-acyl [, preferably ($C_{10}$–$C_{18}$)-fatty acid-acyl].

7. Disaccharide according to claim 6, wherein the acyloxyacyl group is an N-linked 3-hydroxy-($C_{14}$) [3-hydroxy$C_{14}$]-fatty acid-acyl ester-linked at the 3-hydroxy position with a $C_{12}$-fatty acid.

8. Disaccharide according to claim 6, wherein the acyloxyacyl group is an N-linked 3-hydroxy-($C_{14}$)[3-hydroxy$C_{14}$]-fatty acid-acyl ester-linked at the 3-hydroxy position with a $C_{14}$-fatty acid.

9. Disaccharide according to claim 1, wherein $R_2$' is the group Y.

10. Disaccharide according to claim 1, wherein $R_2$ is the group Y.

11. Disaccharide according to claim 1, wherein the 3-hydroxy fatty acid residue is a 3-hydroxy ($C_4$–$C_{24}$)- [, preferably 3-hydroxy ($C_{10}$–$C_{18}$)-fatty acid.

12. Dissacharide according to claim 11, wherein the 3-hydroxy fatty acid residue is a 3-hydroxy-($C_{14}$) [3-hydroxy$C_{14}$]-fatty acid.

13. Disaccharide according to claim 11, wherein $R_2$ is the 3-hydroxy fatty acid residue.

14. Disaccharide according to claim 11, wherein $R_2$' is the 3-hydroxy fatty acid residue.

15. Disaccharide according to claim 1, wherein $R_2$ and $R_2$' are both a group Y.

16. Disaccharide according to claim 15, wherein $R_2$ and $R_2$' are both an acyloxyacyl group comprising an N-linked 3-hydroxy ($C_4$–$C_{24}$)-acyl [, preferably ($C_8$–$C_{18}$)-fatty acid-acyl] ester-linked at the 3-hydroxyl position with a ($C_1$–$C_{20}$)-acyl.

17. Disaccharide according to claim 16, wherein $R_2$ is an N-linked 3-hydroxy-($C_{14}$) [3-hydroxy$C_{14}$]-fatty acid-acyl ester-linked at 3-hydroxy position with a $C_{16}$-fatty acid, and wherein $R_2$' is an N-linked 3-hydroxy-($C_{14}$)[3-hydroxy $c_{14}$]-fatty acid-acyl ester-linked at the 3-hydroxy position with a $C_{12}$-fatty acid.

18. Disaccharide according to claim 1, wherein $R_1$ is a dihydroxyphosphonoyloxy group.

19. Disaccharide according to claim 1, wherein $R_4$ is hydrogen.

20. Disaccharide according to claim 1, wherein $R_1$ is in the α configuration.

21. Disaccharide according to claim 1, wherein $R_3$ is hydrogen.

22. Disaccharide according to claim 1, wherein $R_3$' is hydrogen.

23. Disaccharide according to claim 1, wherein $R_6$' is an hydroxyl group.

24. Disaccharide according to claim 1, wherein $R_4$' is a phosphono group.

25. Disaccharide according to claims 1, wherein the disaccharide is in the salt form comprising one or more cations.

26. Disaccharide according to claim 25, wherein the cations are alkali metal ions.

27. Method for preparing a disaccharide according to claim 1, wherein the Y group is acyloxyacyl comprising the steps of:
 (i) providing a starting material comprising lipid A moiety of lipopolysaccharide-comprising micro-organisms; and
 (ii) subjecting the starting material to an alkaline treatment such that lipid A moiety is O-deacylated at the 3-position and at the 3'-position.

28. Method according to claim 27, wherein the starting material is selected from the group comprising lipopolysaccharide-comprising micro-organisms, Gram-negative bacteria, a surface structure comprising fraction of these micro-organisms and Gram-negative bacteria, or a lipopolysaccharide of these micro-organisms and Gram-negative bacteria.

29. Method according to claim 27, wherein the starting material is lipid A of Gram-negative bacteria.

30. Method according to claim 27, wherein the alkaline treatment is preceded or followed by an acid treatment for removing the core moiety and the polysaccharide side chain.

31. Pharmaceutical composition comprising as an active ingredient a disaccharide according to claim 1, and a pharmaceutically acceptable carrier or diluent.

32. Disaccharide according to claim 6, wherein the group Y is an N-linked 3-hydroxy ($C_8$–$C_{18}$)-fatty acid-acyl ester-linked at the 3-hydroxy position with a ($C_{12}$)-fatty acid-acyl.

33. Disaccharide according to claim 11, wherein the 3-hydroxy fatty acid residue is a 3-hydroxy ($C_{10}$–$C_{18}$)-fatty acid.

34. Disaccharide according to claim 16, wherein $R_2$ and $R_2'$ are both an acyloxyacyl group comprising an N-linked 3-hydroxy ($C_8$–$C_{18}$)-fatty acid-acyl ester-linked at the 3-hydroxy position with a ($C_{10}$–$C_{18}$)-fatty acid-acyl.

\* \* \* \* \*

UNITED STATES PATENT AND TRADEMARK OFFICE
CERTIFICATE OF CORRECTION

PATENT NO. : 6,005,099　　　　　　　　　　　　　Page 1 of 3
DATED : December 21, 1999
INVENTOR(S) : John Gwynfor Davies et al.

It is certified that error appears in the above-identified patent and that said Letters Patent is hereby corrected as shown below:

Title Page, [57] ABSTRACT, line 6, after "treatment such"
　　delete "as" and insert --that the--.

Figure 6:
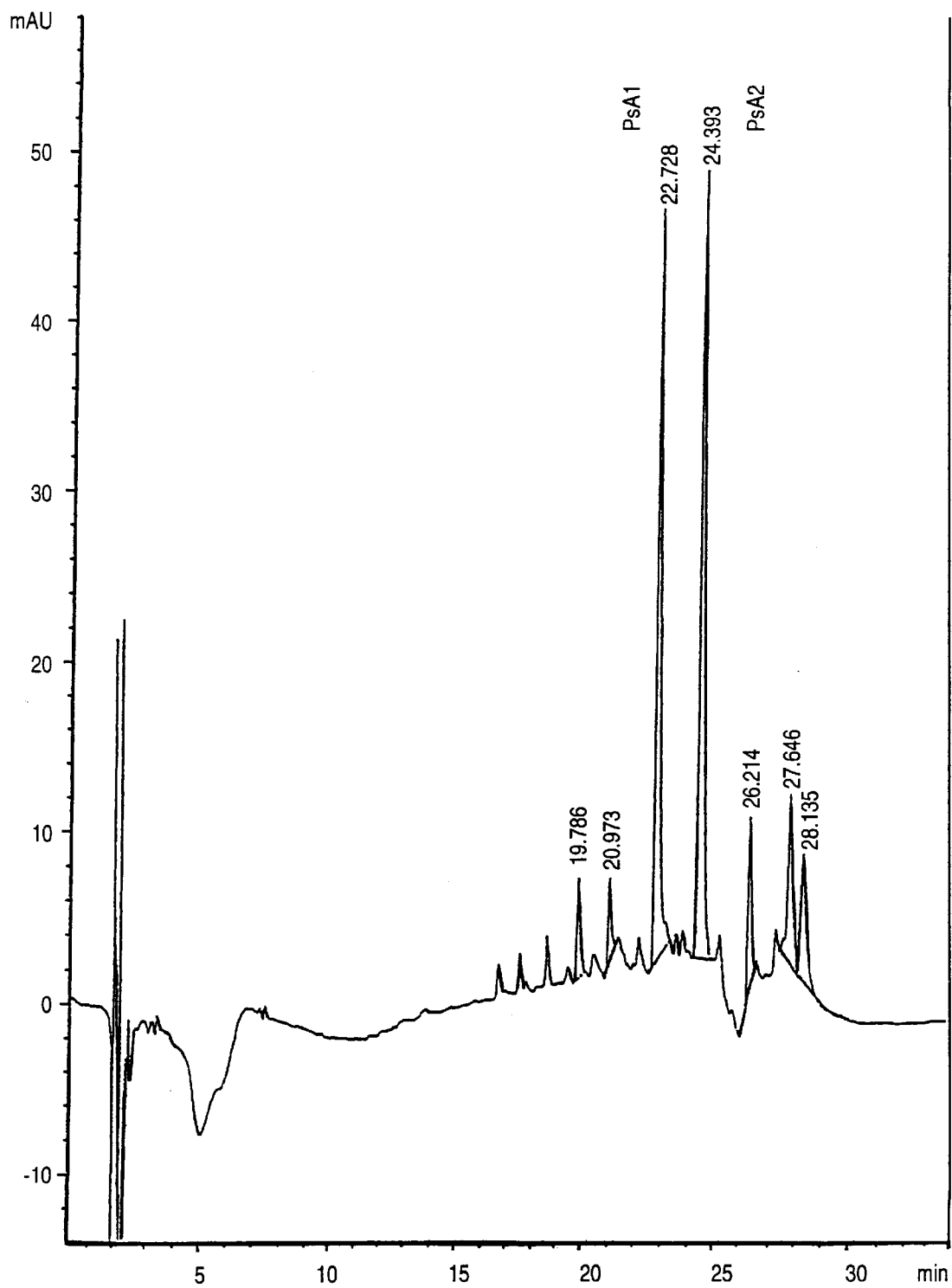
Figure 7:
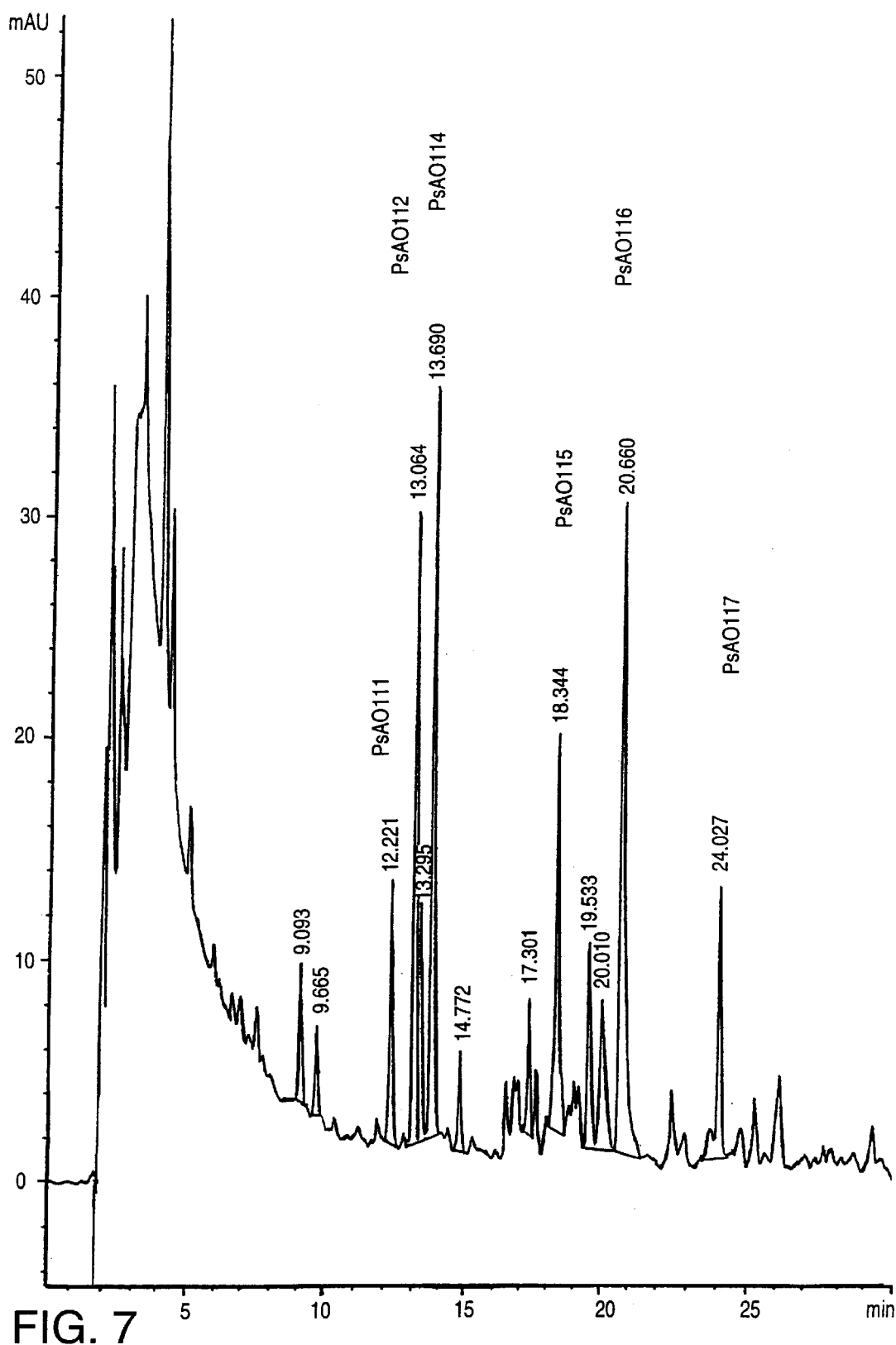

Column 1 after Line 57 insert:
　　-- Brief Description of the Drawings
　　Fig. 1 is a mass spectrum of Disaccharide A showing a
　　molecular peak at 1133.55 mass units;
　　Fig. 2 is a mass spectrum of Disaccharide B showing a
　　molecular peak at 1161.8 mass units;
　　Fig. 3 is an H-NMR-spectrum of Disaccharide A;
　　Fig. 4 shows the $^{13}$C-NMR-spectrum of Disaccharide A (left
　　half, expanded scale);
　　Fig. 5 shows the $^{13}$C-NMR-spectrum of Disaccharide A (right
　　half, expanded scale);
　　Fig. 6 identifies the two major peaks of PsA1 and PsA2
　　representing fatty acids in Ps aeruginosa lipopolysaccharide;
　　Fig. 7 identifies the peaks of PsAO111, PsAO112, PsAO114,
　　PsAO115, PsAO116 and PsAO117; and
　　Fig. 8 shows the quantity of each analogue shown in the
　　legend in a stock solution.
　　　　Detailed Description of the Invention --.

Column 3 Line 54 "position." should read --positions.--.

Column 5 Line 21 "and $R_4$ may" should read --and $R_4$' may--.

Column 16 Line 15, Structural Formula D, refer to center vertical
　　zigzag, insert "O=" at first left point of zigzag.

Columns 19-20, Table 6, refer to row "Lipid A" under column
　　headed "Minimum activity, concentration" delete "0.015"
　　and insert --0.016--.

UNITED STATES PATENT AND TRADEMARK OFFICE
CERTIFICATE OF CORRECTION

PATENT NO. : 6,005,099

DATED : December 21, 1999

INVENTOR(S) : John Gwynfor Davies et al.

It is certified that error appears in the above-identified patent and that said Letters Patent is hereby corrected as shown below:

Column 21 Line 9 "a RIA" should read --an RIA--.

Column 22 Line 27 "6 Weeks" should read --Six weeks--.

Column 22 Line 62 "A dose up of 100" should read --A dose of up to 100--.

Column 23 Line 15 "acatate" should read --acetate--.

Column 23 Line 24 "The adsobed" should read --The adsorbed--.

Column 23 Line 61 "The Sep-Pak's" should read --The Sep-Paks--.

Column 27 Line 17, first column of chart headed "Peak", second row, "PsAOH1" should read --PsAOH2--.

Column 29 Line 51, Claim 6, the following text in brackets should be deleted: --[, preferably $(C_{10}-C_{18})$-fatty acid-acyl]--.

Column 29 Lines 52-53, Claim 6, the following text in brackets should be deleted: --[, preferably $(C_{10}-C_{18})$-fatty acid-acyl]--.

Column 29 Line 57, Claim 7, delete --[3-hydroxy$C_{14}$]--.

Column 29 Lines 60-61, Claim 8, delete --[3-hydroxy$C_{14}$]--.

Column 30 Lines 2-3, Claim 11, delete --[, preferably 3-hydroxy $(C_{10}-C_{18})$]--.

Column 30 Line 7, Claim 12, delete --[3-hydroxy$C_{14}$]--.

Column 30 Lines 18-19, Claim 16, delete --[, preferably $(C_{10}-C_{18})$-fatty acid-acyl]--.

UNITED STATES PATENT AND TRADEMARK OFFICE
CERTIFICATE OF CORRECTION

PATENT NO. : 6,005,099
DATED : December 21, 1999
INVENTOR(S) : John Gwynfor Davies et al.

It is certified that error appears in the above-identified patent and that said Letters Patent is hereby corrected as shown below:

Column 30 Line 24, Claim 17, delete --[3-hydroxy$C_{14}$]--.

Column 30 Line 26, Claim 17, delete --[3-hydroxy$C_{14}$]--.

Column 30 Line 43 "is an" should read --is a--.

Column 30 Line 48, Claim 25, "according to claims 1" should read --according to claim 1--.

Signed and Sealed this

Second Day of January, 2001

Attest:

Attesting Officer

Q. TODD DICKINSON

Commissioner of Patents and Trademarks

UNITED STATES PATENT AND TRADEMARK OFFICE
CERTIFICATE OF CORRECTION

PATENT NO.   : 6,005,099
DATED        : December 21, 1999
INVENTOR(S)  : John G. Davies et al.

It is certified that error appears in the above-identified patent and that said Letters Patent is hereby corrected as shown below:

<u>Title page,</u>
Item [73] Assignee, insert second assignee as follows:
-- Deutsche Om Arzneimittel GmbH, Germany --.

Signed and Sealed this

Ninth Day of October, 2001

*Attest:*

NICHOLAS P. GODICI
*Attesting Officer    Acting Director of the United States Patent and Trademark Office*